(12) United States Patent
Witchey et al.

(10) Patent No.: US 12,727,634 B2
(45) Date of Patent: Sep. 8, 2026

(54) SMART ARTICLE VISUAL COMMUNICATION BASED ON FACIAL MOVEMENT

(71) Applicant: NantWorks, LLC, Culver City, CA (US)

(72) Inventors: Nicholas James Witchey, Laguna Hills, CA (US); Patrick Soon-Shiong, Los Angeles, CA (US)

(73) Assignee: NantWorks, LLC, Culver City, CA (US)

( * ) Notice: Subject to any disclaimer, the term of this patent is extended or adjusted under 35 U.S.C. 154(b) by 0 days.

(21) Appl. No.: 19/226,224

(22) Filed: Jun. 3, 2025

(65) Prior Publication Data

US 2025/0288037 A1 Sep. 18, 2025

Related U.S. Application Data

(63) Continuation of application No. 18/599,796, filed on Mar. 8, 2024, now Pat. No. 12,357,046, which is a (Continued)

(51) Int. Cl.
*A41D 27/08* (2006.01)
*A41D 1/00* (2018.01)
(Continued)

(52) U.S. Cl.
CPC .......... *A41D 27/085* (2013.01); *A41D 1/002* (2013.01); *A41D 13/1192* (2013.01); *A41D 31/305* (2019.02); *A61B 5/6803* (2013.01); *A62B 23/025* (2013.01); *G06F 1/163* (2013.01); *G06F 3/011* (2013.01); *G09G 3/035* (2020.08);
(Continued)

(58) Field of Classification Search
CPC .. A41D 13/11; A41D 13/1192; A41D 27/085; A41D 31/305; A41D 1/002; A61B 5/6803; A62B 18/025; A62B 18/08; A62B 23/025; G09G 2300/026; G09G 2380/02; G09G 2380/08; G09G 3/035; G06F 1/163; G06F 3/011; G06F 3/012
See application file for complete search history.

(56) References Cited

U.S. PATENT DOCUMENTS 6,307,576 B1 10/2001 Rosenfeld
10,891,331 B1 1/2021 Daya et al.
(Continued)

OTHER PUBLICATIONS www.opencv.org (Aug. 7, 2020).
(Continued)

*Primary Examiner* — Robin J Mishler
(74) *Attorney, Agent, or Firm* — Harness Dickey & Pierce P.L.C.

(57) ABSTRACT

A smart mask includes a first material layer, at least one display, a first sensor, and a control module. The first material layer is configured to cover a portion of a face of a person. The at least one display is connected to the first material layer and configured to display images over a mouth of the person. The first sensor is configured to detect movement of the mouth of the person and generate a signal indicative of the movement of the mouth. The control module is configured to receive the signal and display the images on the display based on the movement of the mouth.

18 Claims, 13 Drawing Sheets

Related U.S. Application Data continuation of application No. 18/234,698, filed on Aug. 16, 2023, now Pat. No. 11,974,619, which is a continuation of application No. 17/892,256, filed on Aug. 22, 2022, now Pat. No. 11,864,606, which is a continuation of application No. 17/481,723, filed on Sep. 22, 2021, now Pat. No. 11,457,680, which is a continuation of application No. 16/990,781, filed on Aug. 11, 2020, now Pat. No. 11,160,319.

(51) Int. Cl.

| | |
|---|---|
| ***A41D 13/11*** | (2006.01) |
| ***A41D 31/30*** | (2019.01) |
| ***A61B 5/00*** | (2006.01) |
| ***A62B 23/02*** | (2006.01) |
| ***G06F 1/16*** | (2006.01) |
| ***G06F 3/01*** | (2006.01) |
| ***G09G 3/00*** | (2006.01) |
| ***G10L 15/08*** | (2006.01) |

(52) U.S. Cl.

CPC ... *G09G 2300/026* (2013.01); *G09G 2380/02* (2013.01); *G09G 2380/08* (2013.01); *G10L 15/08* (2013.01)

(56) References Cited

U.S. PATENT DOCUMENTS

| | | | | |
|---|---|---|---|---|
| 11,160,319 | B1 | 11/2021 | Witchey et al. | |
| 2016/0029716 | A1* | 2/2016 | Duncan | A41D 13/11 128/863 |
| 2016/0041581 | A1* | 2/2016 | Piccionelli | G09F 21/048 345/156 |
| 2018/0225988 | A1* | 8/2018 | Morgado | G09B 21/009 |
| 2019/0035153 | A1* | 1/2019 | Dange | G06V 20/20 |
| 2019/0060682 | A1 | 2/2019 | Mou et al. | |
| 2019/0347817 | A1 | 11/2019 | Ferrantelli et al. | |
| 2021/0081749 | A1* | 3/2021 | Claire | G06F 3/005 |
| 2021/0244109 | A1 | 8/2021 | Nishida | |
| 2022/0047021 | A1 | 2/2022 | Witchey et al. | |
| 2022/0395041 | A1 | 12/2022 | Witchey et al. | |
| 2024/0125189 | A1 | 4/2024 | Sherrill et al. | |

OTHER PUBLICATIONS www.adafruit.com/product/1755 (Aug. 7, 2020).

www.adafruit.com/product/158 (Aug. 7, 2020).

www.adafruit.com/product/519 (Aug. 7, 2020).

www.bendlabs.com/products/ (Aug. 7, 2020).

www.adafruit.com/category/65 (Aug. 7, 2020).

www.dyslexia-reading-well.com/44-phonemes-in-english.html, Copyright 2013-2020 © by Michael Bates, Dyslexia-Reading-Well.com (Aug. 7, 2020).

en.wikipedia.org/wiki/Phoneme (Aug. 7, 2020).

ibug.doc.ic.ac.uk/resources/facial-point-annotations/, Intelligent Behavior Understanding Group (IBUG), Department of Computing, Imperial College London (Aug. 7, 2020).

www.rose-medical.com/mouth-positions.html, Copyright © 2020 Rose Medical Solutions Ltd. (Aug. 7, 2020).

https://www.conductivetech.com/products/flexible-printed-circuitry/ , Conductive Technologies Inc®, ISO 13486/ISO 0001 Certified (Aug. 7, 2020).

https://www.cheaptubes.com/graphene-sensors/ (Aug. 7, 2020).

https://stretchsense.com/sensors/ (Aug. 7, 2020).

https://starboardmedical.com/skin-sensors/, Copyright 2019 Starboard Medical, Inc (Aug. 7, 2020).

https://newvisiondisplay.com/6-flexible-amoled/, May 11, 2018, © 2012-2020 New Vision Display (Shenzhen) Technology Co, Ltd. (Aug. 7, 2020).

www.raspberripi.org, Raspberry PI Foundation, UK Registered Charity 1129409 (Aug. 7, 2020).

https://www.tekscan.com/products-solutions/electronics/flexiforce-oem-development-kit, Tekscan Medical Devices, South Boston, MA, Pressure Mapping, Force Measurement & Tactile Sensors (Aug. 7, 2020).

https://www.tekscan.com/products-solutions/electronics/flexiforce-oem-development-kit, © Tekscan Inc., 2020, FlexiForce™ Prototyping Kit, ISO 9001-2008 Compliant & 13485:2016 Registered, DS Rev 072720 (Aug. 7, 2020).

Compression Sensing Element, #OSEC—Compression Sensing Element, Version 27082018, Technical Data Sheet, StretchSense™ (Aug. 7, 2020).

Frontiers in Chemistry, Published Jun. 2019, vol. 7, Article 399, "Graphene-Based Sensors for Human Health Monitoring" by Haizhou Huang, Shi Su, Nan Wu, Hao Wan, Shu Wan, Hengchang Bi, and Litao Sun.

https://www.dezeen.com/2020/03/06/guardian-g-volt-face-mask-graphene-coronavirus-bacteria, Guardian G-Volt masks use graphene and electrical charge to repel viruses (May 14, 2020).

https://www.crystalfontz.com/product/cfal16032a0018pw-flexible-oled-display-160x32 (Aug. 7, 2020).

https://www.directa-plus.com/, © 2019 Directa Plus S.p.A. (Aug. 7, 2020).

https://www.matexcel.com/category/products/graphene/, Matexcell, Bohemia, NY, Copyright © 2007-2020 Matexcel, (Aug. 7, 2020).

https://www.nature.com/articles/s41528-019-0061-5, Nature Partner Journals (NPJ), Fleible Electronics, "Wearable multifunctional printed graphene sensors," by Altynay Kaidarova, Mohammed Asadullah Khan, Marco Marengo, Liam Swanepoel, Alexander Przybysz, Cobus Muller, Andreas Fahlman, Ulrich Buttner, Nathan R. Geraldi, Rory P. Wilson, Carlos M. Duarte, and Jurgen Kosel; Published online Aug. 2, 2019.

https://www.omegapiezo.com/strip-actuators-bimorph-equivalent/, Omega Piezo Technologies © (Aug. 7, 2020).

https://www.sciencedirect.com/science/article/abs/pii/S0165993617300031, TrAC Trends in Analytical Chemistry, vol. 91, Jun. 2017, pp. 53-66, "Graphene based sensors nad biosensors," by Celine I.L. Justino, Ana R. Gomes, Ana C. Freitas, Armando C. Duarte, Teresa A.P. Rocha-Santos.

MDPI, Nanomaterials 2019, 9, 496; doi:10.3390/nano9040496, "Flexible and Highly Sensitive Pressure Sensors Based on Microstructured Carbon Nanowalls Electrodes," by Xi Zhou, Yongna Zhang, Jun Yang, Jialu Li, Shi Luo, and Dapeng Wei, Published Apr. 1, 2019.

MDPI, Nanomaterials 2019, 9, 737; doi:10.3390/nano9050737, "Antibacterial Properties of Graphene-Based Nanomaterials," by Parveen Kumar, Peipei Huo, Rongzhao Zhang, and Bo Liu, Published May 13, 2019.

MDPI, Sensors 2018, 18, 645; doi:10.3390/s18020645, "Flexible, Stretchable Sensors for Wearable Health Monitoring: Sensing Mechanisms, Materials, Fabrication Strategies and Features," by Yan Liu, Hai Wang, Wei Zhao, Min Zhang, Hongbo Qin, and Yongqiang Xie, Published Feb. 22, 2018.

StretchSense 3-Channel Silicone Sensor Product, StretchSense™.

StretchFabric Sensing Element (SSD18), Technical Datasheet, Version 20122018, StretchSense™.

www.arduino.cc (Aug. 7, 2020).

Office Action from corresponding U.S. Appl. No. 16/990,781 dated Dec. 28, 2020.

Office Action from corresponding U.S. Appl. No. 16/990,781 dated Mar. 29, 2021.

Office Action from corresponding U.S. Appl. No. 17/481,723 dated Apr. 20, 2022.

Office Action from corresponding U.S. Appl. No. 18/234,698, dated Oct. 13, 2023.

Office Action from corresponding U.S. Appl. No. 18/234,698 dated Nov. 28, 2023.

Office Action from U.S. Appl. No. 18/599,796 dated Jan. 16, 2025.

Office Action from U.S. Appl. No. 18/599,796 dated Mar. 17, 2025.

* cited by examiner 700
704
702

804
800
808
806
602
802

604
600
610
608
606
602

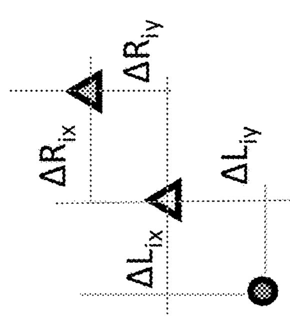
FIG. 16D
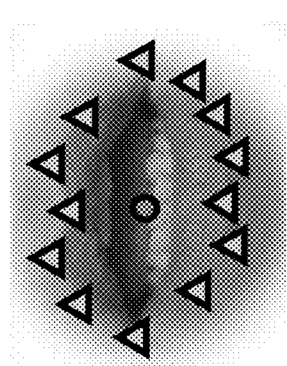
FIG. 16C
Landmark in Neutral Position
Origin
FIG. 16B
FIG. 16A

SMART ARTICLE VISUAL COMMUNICATION BASED ON FACIAL MOVEMENT

CROSS-REFERENCE TO RELATED APPLICATIONS

This application is a continuation of U.S. patent application Ser. No. 18/599,796, filed on Mar. 8, 2024, which is a continuation of U.S. patent application Ser. No. 18/234,698, filed on Aug. 16, 2023, which is a continuation of U.S. patent application Ser. No. 17/892,256, filed on Aug. 22, 2022, which is a continuation of U.S. patent application Ser. No. 17/481,723, filed on Sep. 22, 2021, which is a continuation of U.S. patent application Ser. No. 16/990,781, filed on Aug. 11, 2020. The entire disclosures of each of the above applications are incorporated herein by reference.

FIELD

The present disclosure relates to clothing technologies with embedded electronics and more particularly to electronics-augmented face masks.

BACKGROUND

During a pandemic, people are often isolated to prevent the spread of, for example, viral and/or bacterial infections. People may wear face masks to reduce risk of infection themselves and/or to reduce risk of infecting others. Wearing of face masks can become widespread during a pandemic, such that many institutions (e.g., retail shops, stores, services, etc.) will not allow people to enter the institutions unless they are wearing a face mask, whether as a corporate decision or as a legal requirement.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

All external document references are incorporated by reference in their entirety.

SUMMARY

A smart mask includes a first material layer, at least one display, a first sensor and a control module. The first material layer is configured to cover a portion of a face of a person. The at least one display is connected to the first material layer and configured to display images over a mouth of the person. The first sensor is configured to detect movement of the mouth of the person and generate a signal indicative of the movement of the mouth. The control module is configured to receive the signal and display the images on the display based on the movement of the mouth.

In other features, the smart mask further includes a second material layer, a third material layer, and a power source. The power source is connected to the second material layer and powering the control module. The first sensor is connected to the third material layer. The signal is indicative of movement of a first portion of the mouth of the person. The control module is configured to display the images on the display based on the signal.

In other features, the first sensor includes an adhesive layer for attaching to the face of the person. In other features, the smart mask further includes a second sensor configured to generate a signal indicative of movement of a second portion of the mouth. The control module is configured to display the images on the display based on the signal indicative of the movement of the second portion of the mouth.

In other features, the at least one display is embedded in the first material layer or overlaid on the first material layer. In other features, the at least one display is disposed in one or more pockets on the first material layer.

In other features, the at least one display includes multiple displays. Each of the displays is configured to display one or more images based on the detected movement of the mouth. In other features, the at least one display is perforated.

In other features, the smart mask further includes a second material layer and spacers disposed to separate the at least one display from the second material layer. In other features, the smart mask further includes multiple layers including the first material layer. The layers include channels for air flow.

In other features, the smart mask further includes a filter including multiple sensors including the first sensor. The sensors are configured to generate signals indicative of facial movements of the person including the movement of the mouth or of utterances. The control module is configured to display the images based on the signals received from the sensors.

In other features, the first sensor is a graphene sensor. In other features, the smart mask further includes multi-purpose sensors, where each of the multi-purpose sensors include antimicrobial material capable of generating a sensor signal (e.g., resistance, capacitance, current, voltage, etc.). In other features, at least one of the multi-purpose sensors includes graphene-based nanomaterials having antibacterial features. In other features, the multi-purpose sensors include at least one of a nanotube sensor or a graphene health sensor.

In other features, the at least one display includes light emitting diodes. The light emitting diodes are arranged to track movements of the mouth. The images are low resolution images generated by the light emitting diodes.

In other features, the smart mask further includes an audio sensor configured to detect sounds or utterances generated by the mouth of the person. The control module is configured to display the images based on the detected sounds.

In other features, the control module is configured to perform an artificial training process or method with one or more devices such that at least one of the control module or the one or more devices are able to map detected facial movements of the person to the images for display on the at least one display.

In other features, a system includes a first article and a second article. The first article includes a first material layer, at least one sensor and a control module. The at least one sensor is connected to the first material layer and configured to generate a sensor signal indicative of at least one movement of a mouth of a person or sound generated via the mouth of the person. The control module is configured to transmit the sensor signal from the first article indicating the at least one movement of the mouth of the person or sound generated via the mouth of the person. The second article is separate from the first article and includes a second material layer, a transceiver and at least one display. The second material layer configured to cover a portion of a body of the person. The transceiver is configured to receive the sensor signal. The at least one display is connected to the second material layer and configured to display images on the at least one display based on the at least one movement of the mouth of the person or sound generated via the mouth of the person.

In other features, the first article is a mask. In other features, the second article is a mask. In other features, the images include at least one of images of the mouth or other images (e.g., cartoon characters, emoticons, text, sign language graphics, etc.).

In other features, a smart article is provided and includes a first material layer, at least one display and a control module. The first material layer is configured to cover a portion of a body of a person. The at least one display is connected to the first material layer and configured to display images. The control module is configured to detect movement of a mouth of the person and display the images on the display based on or in response to the movement of the mouth.

In other features, the smart article further includes a second material layer, a third material layer, and a power source. The power source is connected to the second material layer and powering the control module. The first sensor is connected to the third material layer and configured to generate a signal indicative of movement of a first portion of the mouth of the person. The control module is configured to display the images on the display based on the signal.

In other features, the first sensor comprises an adhesive layer for attaching to a face of the person. In other features, the smart article further includes a second sensor configured to generate a signal indicative of movement of a second portion of the mouth. The control module is configured to display the images on the display based on the signal indicative of the movement of the second portion of the mouth.

In other features, the at least one display is embedded in the first material layer or overlaid on the first material layer. In other features, the at least one display is disposed in one or more pockets on the first material layer.

In other features, the at least one display includes multiple displays. Each of the displays is configured to display one or more images based on the detected movement of the mouth. In other features, the at least one display is perforated or porous.

In other features, the smart article further includes a second material layer and spacers. The spacers are disposed to separate the at least one display from the second material layer. In other features, the smart article further includes layers including the first material layer. The layers include channels for air flow.

In other features, the smart article further includes a filter including sensors. The sensors are configured to generate signals indicative of facial movements of the person including the movement of the mouth. The control module is configured to display the images based on the signals received from the plurality of sensors.

In other features, the smart article further includes at least one graphene sensor configured to generate a signal indicative of the movement of the mouth. The control module is configured to display the images on the display based on the signal.

In other features, the at least one display includes light emitting diodes. The light emitting diodes are arranged to track movements of the mouth. The images are low resolution images generated by the light emitting diodes.

In other features, the at least one display includes light emitting diodes configured to track movements of the mouth.

In other features, the smart article further includes an audio sensor configured to detect sounds generated by the mouth of the person. The control module is configured to display the images based on the detected sounds.

In other features, the control module is configured to perform an artificial training process with one or more devices such that at least one of the control module or the one or more devices are able to map detected facial movements of the person to the images for display on the at least one display.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 16A is a front view of a mouth of a person in a silent and neutral position.

FIG. 16B is a front view of the mouth of FIG. 16A with overlaid landmarks and an origin in accordance with the present disclosure.

FIG. 16C is a front view of the mouth of FIG. 16A with the overlaid landmarks of FIG. 16B moved to different locations associated with mouth movement and relative to the origin in accordance with the present disclosure.

FIG. 16D is an example diagram illustrating positioning of landmarks relative to the origin in accordance with the present disclosure.

In the drawings, reference numbers may be reused to identify similar and/or identical elements.

DETAILED DESCRIPTION

While face masks aid in protecting people from air-borne diseases, face masks often interfere with person-to-person communication. For example, a face mask can hide significant portions of a face of a person speaking, which can interfere with the ability of others to interpret the facial expressions of the person speaking. This limited ability to see and interpret facial expressions also limits the full breadth of communication.

The examples set forth herein include smart masks and other smart articles. As used herein, the term "article" refers to any wearable element, such as pants, hats, shirts, gloves, shoes, etc. or portions thereof. A smart article may include one or more sensors for detecting body movements, such as and including mouth and/or cheek movements, and one or more displays for displaying images and/or video of a corresponding person's face showing movements of the person's face as the movements occur (i.e., in real-time). Each smart article may also include one or more other sensors, such as audio sensors for detecting verbal sounds created by the person, strain sensors, compression sensor, piezoelectric sensors, thermal sensors, or other types of sensor. The smart article or other device in communication with the smart article may map data received from the sensors to body movements, facial movements for example and display the facial movements on an electronic display.

As an example, a face mask (hereinafter referred to as a "mask") or mask overlay may display a digital representation of a person's face, where the digital representation includes a rendering that mimics or matches the person's face movements as the person speaks and/or emotes. This aids a person listening to the speaker in interpreting the speaker. A high-level example for rendering an image on a mask includes: creating a digital and flexible display overlay that fits over a mask (or as part of a mask); attaching the display to the mask; connecting an article control module to the display; and showing on the display in at least near real-time what the person's face and/lips are doing including movements of lips, tongue, cheeks, nose, etc. The display may with sufficient resolution render what the person's actual face looks like while the person speaks, utter sounds, and/or emotes.

Figure 1:
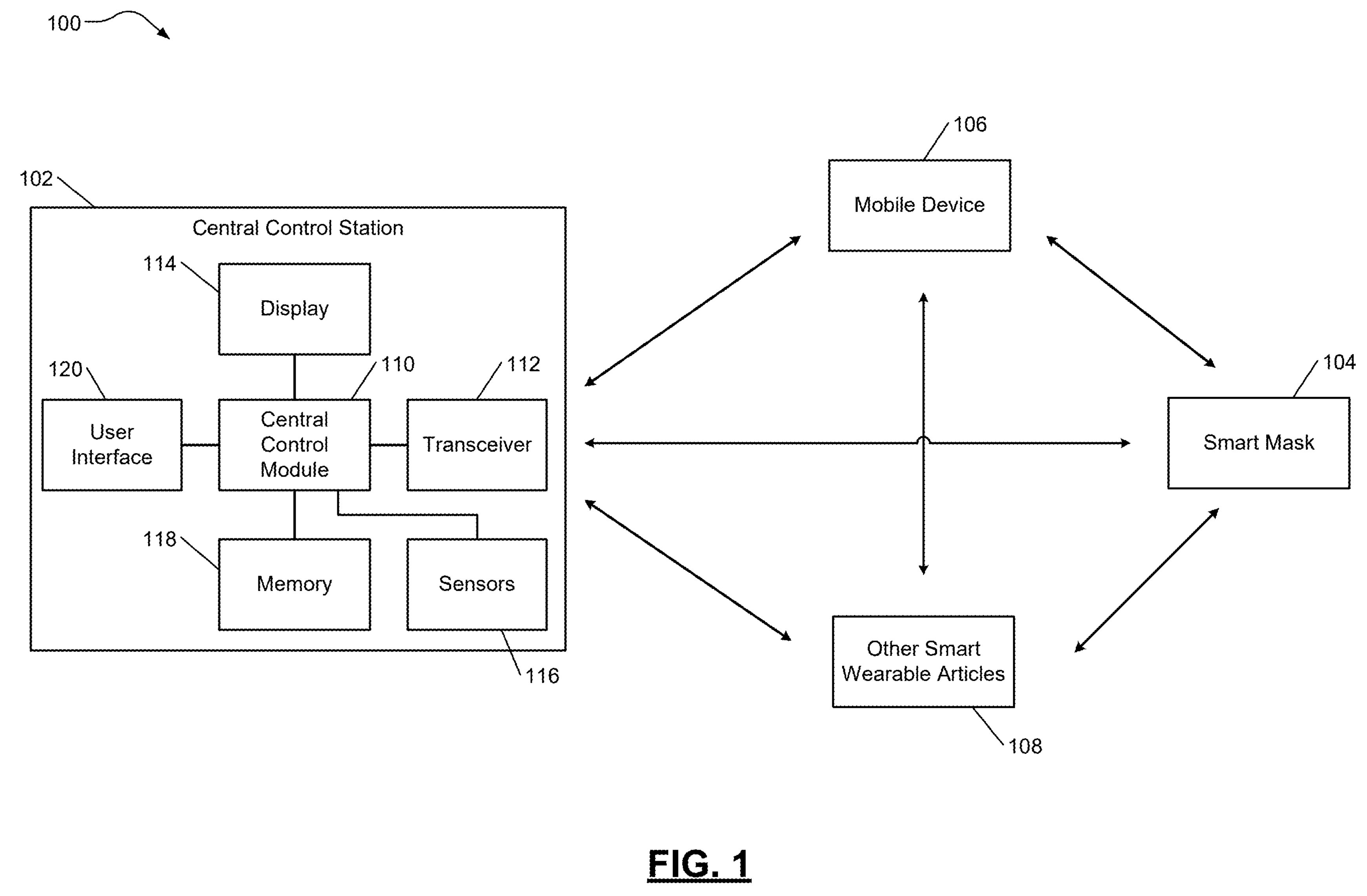
FIG. 1 is a functional block diagram of an example smart mask ecosystem in accordance with the present disclosure.
Figure 2:
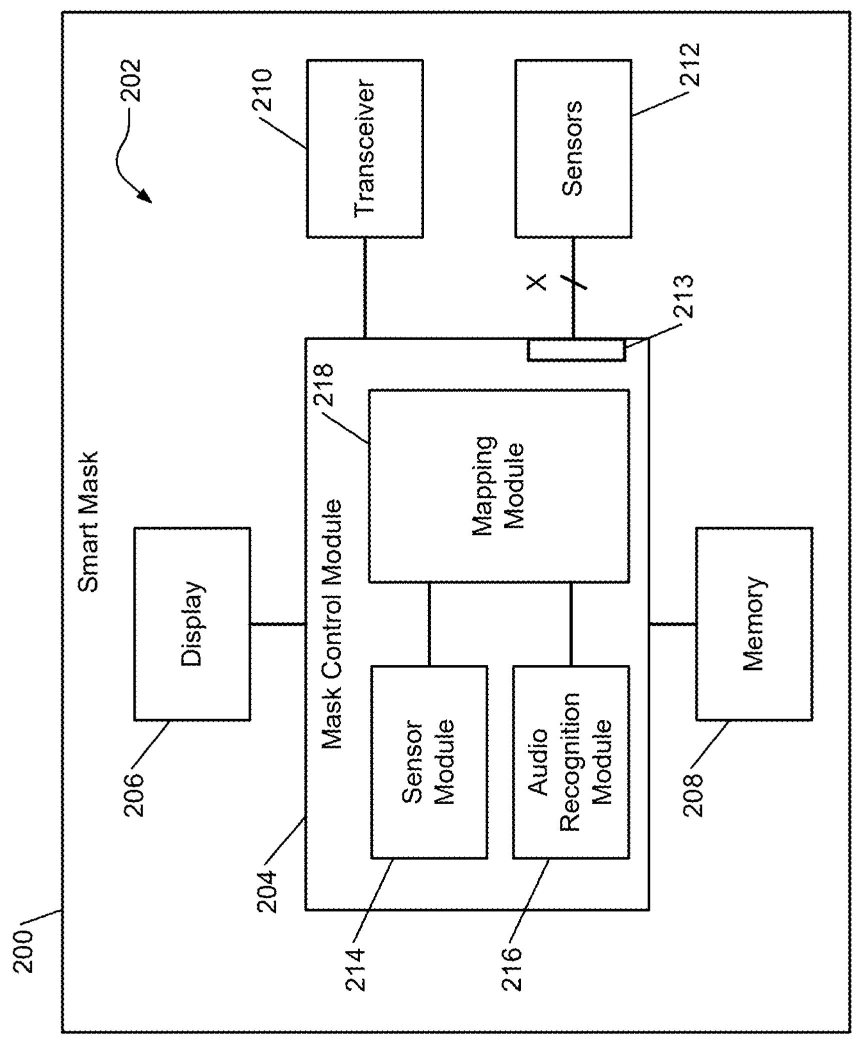
FIG. 2 is a functional block diagram of an example smart mask having a smart mask visual communication system in accordance with the present disclosure.
Figure 3:
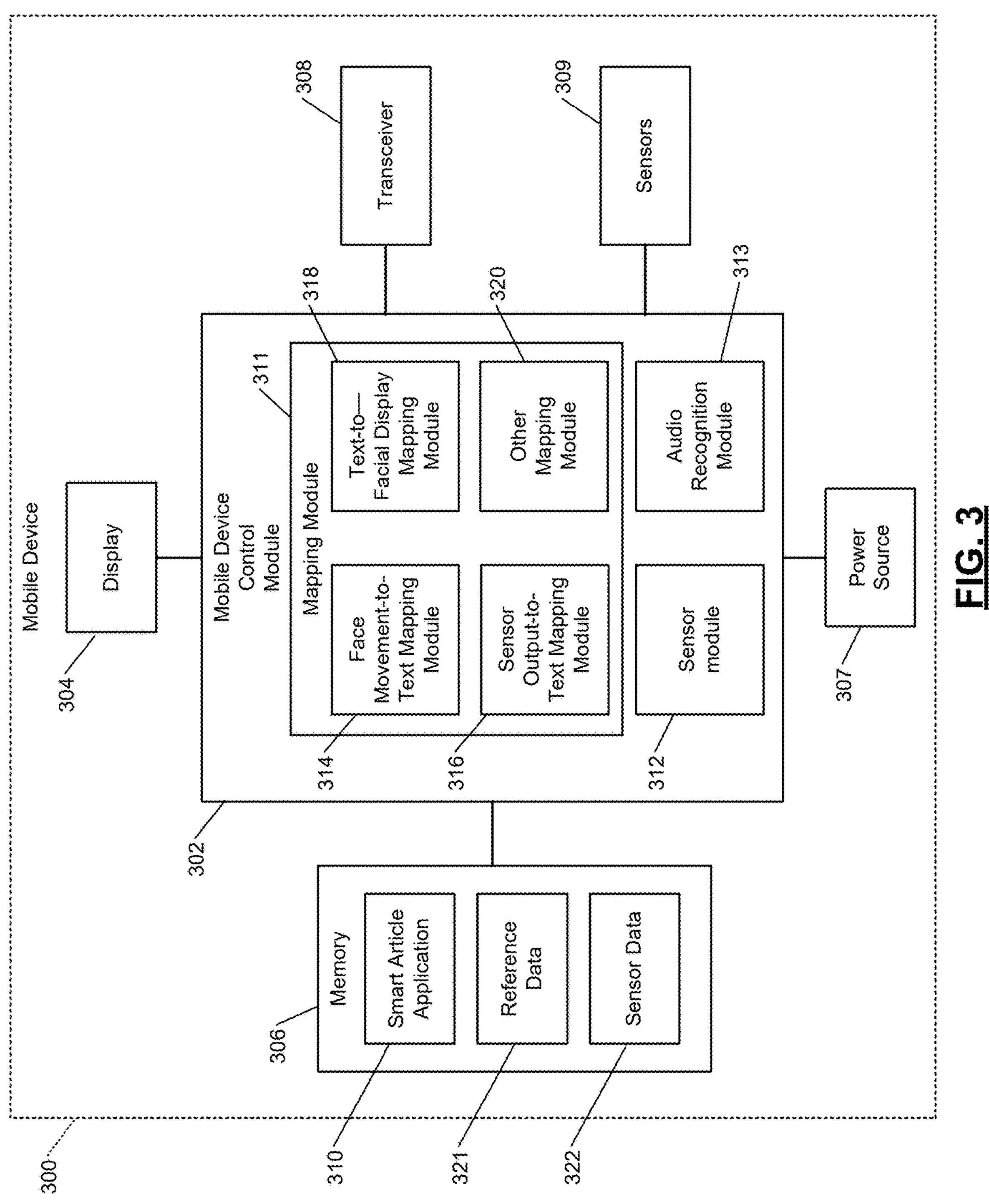
FIG. 3 is a functional block diagram of an example mobile device implementing a smart mask application in accordance with the present disclosure.
Figure 4:
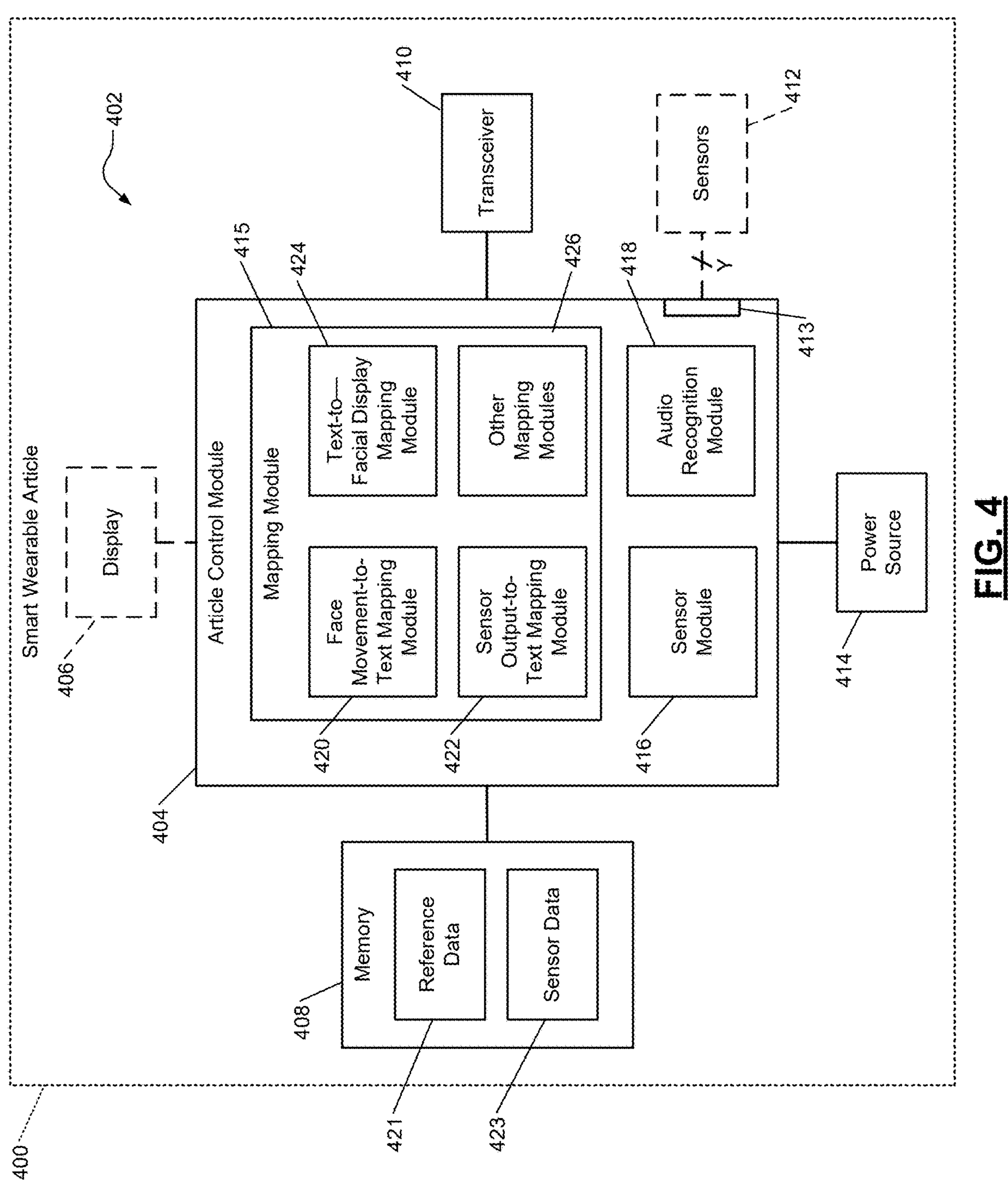
FIG. 4 is a functional block diagram of an example smart wearable article in accordance with the present disclosure.

FIG. 1 shows an example smart mask ecosystem 100 that may include a central control station 102, a smart mask 104, a mobile device 106, and one or more other smart wearable articles 108. The central control station 102 may communicate with any of the smart mask 104, the mobile device 106 and the smart wearable articles 108 as further described below in association with the examples of FIGS. 2-19. The central control station 102 may include a central control module 110, a transceiver 112, a display 114, sensors 116, a memory 18 and a user interface 120. The central control module 110 may collect sensor data, map the data to facial movements and provide results of the mapping to and of the devices 104, 106, 108. The central control module 110 communicates with the devices 104, 106, 108 via the transceiver 112. The memory 118 may store software for mapping the sensor data disclosed herein. Example mapping modules and applications are shown in FIGS. 2-4 with respect to the devices 104, 106, 108 and described below and may be similarly implemented in the central control station 102. The mapping software is executed by the central control module 110.

The sensors 116 may include various types of sensors capable of acquiring one or more modalities of sensor data. Example sensors can include one or more cameras, audio sensors (e.g., microphones), thermal sensors, accelerometers, and/or other sensors for detecting and/or recording facial movements. Audio and video may be initially recorded for a person and stored as a reference (or reference data) and used for future mapping as discussed further below. Additional real-time audio may also be detected during subsequent use and used for mapping facial movements while a person is, for example, speaking. The reference data, the real-time audio and/or other data collected by the devices 104, 106, 108 may be translated to facial movements and provided to the devices 104, 106, 108 for display an electronic display on one or more of the devices 104, 106, 108. Some or all of the mapping may occur at any of the devices 104, 106, 108 as described below. Examples of the devices 104, 106, 108 are shown and described with respect to FIGS. 2-19.

The display 114 may be a touchscreen or other type of display. The sensors 116 may include audio sensors, cameras, accelerometers, etc. The sensors 116 may be used for recording and training purposes and/or for mapping purposes as further described below.

FIG. 2 shows an example smart mask 200 that may represent the smart mask 104 of FIG. 1 and includes a smart mask visual communication system 202. The smart mask visual communication system 202 may include a mask control module 204, one or more displays (one display 206 is shown in FIG. 2), a memory 208, a transceiver 210 and one or more sensors 212. The mask control module 204 may include an interface 213, a sensor module 214, an audio recognition module 216 and a mapping module 218. The interface 213 may include channels connected to the sensors 212. The interface 213 may include one or more channels connected respectively to one or more sensors, where X refers to the number of channels and represents any practical number of channels (e.g., at least 1 channel, at least 2 channels, at least 10 channels, and so on) as required by the desired implementation.

The sensor module 214 may collect sensor data from the sensors 212 and/or from any other devices in the ecosystem 100 of FIG. 1. The audio recognition module 216 may execute audio recognition software to translate detected audio into text, which may then be used by the mapping module 218 for mapping sensor data to image data for display on the display 206, one or more other displays of the smart mask and/or other device (e.g., smart articles) of the ecosystem 100. The mapping module 218 may map sensor data to image data for display on one or more displays. This may include mapping detected movements to display data, which may be based on the output of the audio recognition module 216. The transceiver 210 may be used to communicate with any of the devices in the ecosystem 100. One should appreciate the selection of images to display can depend on one or more sensor data modalities (e.g., audio data, stress sensor data, strain sensor data, thermal data, pressure sensors, etc.).

As an example, several small sensors may be included that are able to sense movement of the mask while a person is talking or emoting. The sensors 212 may include piezoelectric sensors, thermal sensor, stretch sensors, etc. As another example, a predetermined number of sensors (e.g., four sensors) may be included; one attached to each of the strings of the mask. The sensors 212 may include sensors that attach to a person's face. The sensors 212 may be disposed in material (or layers) of the mask 200. In one embodiment, sensors are included in or operate as one or more filters of the mask 200.

FIG. 3 shows an example mobile device 300 may represent the mobile device 106 of FIG. 1 and may include a mobile device control module 302, a display 304, a memory 306, a power source 307, a transceiver 308 and sensors 309. The mobile device 300 may be a cell phone, a laptop computer, a tablet, a wearable device (e.g., a smart watch), a dedicated mask controller, etc. The mobile device control module 302 executes a smart article application 310 for mapping collected data to facial movement images. The mobile device control module 302 may include a mapping module 311, a sensor module 312 and/or an audio recognition module 313. The mapping module 311 may be referred to as a classifier and include a face movement-to-text mapping module 314, a sensor output-to-text mapping module 316, a text-to-facial display mapping module 318, and other mapping modules 320, which may be implemented as part of the smart article application 310. Thus, mapping module 316 is considered to convert one or more sensor modalities to one or more other display modalities (e.g., 2D digital rendering of a face, 3D digital rendering of a face, displayed text, displayed sign language, displayed emoticons, displayed emotes, etc.).

The modules 311, 312, 313, 314, 316, 318, 320 are provided as examples only, the mobile device 300 may include other modules. The face movement-to-text mapping module 314 may map detected face movements, which may be based on data received from other devices (e.g., one or more of the devices 104, 108 of FIG. 1), to text. The sensor output-to-text mapping module 316 may map data from sensors 309 and/or sensors of other devices (e.g., one or more of the devices 104, 108 of FIG. 1) to text. The text-to-facial display mapping module 318 may map the text from the modules 314, 316 to facial images to display. One of the other mapping modules 320 may map received and collected data directly to facial images. The described mappings may be based on reference data 321 and the collected sensor data (designated 322) stored in the memory 306. Based on this example, one should appreciate the mapping can include a direct mapping of the sensor data to image data (i.e., audio-to-image) or an indirect mapping to image data via another data modalities (i.e., audio-to-text and then text-to-image).

The sensor module 312 may collect sensor data from the sensors 309 and/or from any other device in the ecosystem 100 of FIG. 1. The audio recognition module 313 may execute audio recognition software to translate detected audio into text, which may then be used by the mapping module 311 for mapping sensor data to image data for display on the display 304, one or more other displays of a smart mask, one or more displays of smart articles, and/or other device of the ecosystem 100. Example techniques that can be adapted for use with audio recognition or language recognition includes those disclosed in one or more of U.S. Pat. Nos. 10,347,240; 8,229,728; 8,374,871; 8,478,578; 8,583,416; and 9,026,441. The mapping module 311 may map sensor data to image data for display on one or more displays. This may include mapping detected movements to display data, which may be based on the output of the audio recognition module 313. The transceiver 308 may be used to communicate with any of the devices in the ecosystem 100.

The display 304 may be a touchscreen and/or other type of display. The sensors 309 may include audio sensors, cameras, accelerometers, location sensors, etc. The sensors 309 may be used for recording and training purposes and/or for mapping purposes as further described below.

FIG. 4 shows an example smart wearable article 400, which may represent any of the smart mask 104 and smart articles 108 of FIG. 1. The smart wearable article 400 may include a smart mask visual communication system 402, which may include an article control module 404, one or more displays (one display 406 is shown in FIG. 4), a memory 408, a transceiver 410, one or more sensors 412 and a power source 414. The article control module 404 may be suitable for wearable implementations and be based on wearable technologies. The article control module 404 may have a computing platform specifically suited for being sown into clothing or fabric.

A smart mask device may include a smart mask controller operating based on a computing platform highly suitable for wearable technologies. A couple of examples include the Raspberry PI computing platform (see URL www.raspberrypi.org) and the Arduino computing platform (see URL www.arduino.cc). Still further, a computing platform that is specifically suited for being sown into clothing or fabric includes the wearable controller offered by Adafruit and based on the Arduino platform (see URL www.adafruit.com/category/65).

The article control module 404 may include an interface 413, a mapping module 415, a sensor module 416, and an audio recognition module 418. The mapping module 415 may be referred to as a classifier and include a face movement-to-text mapping module 420, a sensor output-to-text mapping module 422, a movement-to-image mapping module, a text-to-facial display mapping module 424 and/or other mapping modules 426.

The interface 413 may include channels connected to the sensors 412. The interface 413 may include one or more channels connected respectively to one or more sensors, where Y refers to the number of channels.

The modules 404, 415, 416, 418, 420, 422, 424, 426 are provided as examples only, the smart wearable article 400 may include other modules. The face movement-to-text mapping module 420 may map detected face movements, which may be based on data received from other devices (e.g., one or more of the devices 104, 108 of FIG. 1), to text. The sensor output-to-text mapping module 422 may map data from sensors 412 (e.g., one or more of the devices 104, 108 of FIG. 1) to text. The text-to-facial display mapping module 424 may map the text from the modules 420, 422 to facial images to display. One of the other mapping modules 426 may map received and collected data directly to facial images. The described mappings may be based on reference data 421 and the collected sensor data (designated 423) stored in the memory 408. Although some embodiments leverage a movement to text mapping module, it should be appreciated that other embodiments map movements to images.

The sensor module 416 may collect sensor data from the sensors 412 and/or from any other devices in the ecosystem 100 of FIG. 1. The audio recognition module 418 may execute audio recognition software to translate detected audio into text, which may then be used by the mapping module 415 for mapping sensor data to image data for display on the display 406 one or more other displays of the smart mask and/or other device of the ecosystem 100. The mapping module 415 may map sensor data directly or indirectly to image data for display on one or more displays. This may include mapping detected movements to display data, which may be based on the output of the audio recognition module 418. The transceiver 410 may be used to communicate with any of the devices in the ecosystem 100.

Referring again to FIGS. 1-4, the smart masks disclosed herein may render an image output of a portion of a person's face thereby allowing others to see, for example, the person's mouth, cheeks and/or nose move or possibly see the person's emotes. Each smart mask and smart article (or article) may be referred to as a computing device having a control module (e.g., a control circuit and/or processor, FPGA, ASIC, GPU, etc.) and memory. The control module executes software instructions stored in a non-transitory computer readable memory (e.g., RAM, ROM, flash, SSD, HDD, etc.) to perform operations disclosed herein. The articles may include an electronic display that generates an output based on sensor data received via sensors. In addition to including interfaces for sensors, the control modules and/or articles may include interfaces for other devices, such as transceivers. The transceivers may be used for data uploads, downloads, and/or other communication signals. The communication interfaces may include wired interfaces (e.g., universal serial bus (USB), recommended standard (RS)-232, general purpose input output (GPIO), etc.) or wireless interfaces (e.g., 802.11, wireless gigabit (WiGIG), BlueTooth®, Zigbee®, near-field communication (NFC), etc.).

In some embodiments, multiple articles may cooperate together, possibly via wireless computing channels (e.g., Institute of Electrical and Electronic Engineers (IEEE®) 802.11, WiGIG, BlueTooth®, Zigbee®, NFC, etc.). As another example, the articles may each include a single set of elements directly wired together; the display, the sensors, a small processor, and a wireless interface. As disclosed the corresponding ecosystem may include a smart phone with a smart mask (or article) application that is used to communicate with the control modules of the articles via the wireless interface. The control modules may receive the sensor inputs, transform the inputs to display outputs, and then display the outputs on one or more displays. Further, some embodiments may exist within a personal area network (PAN) where the various elements of the inventive technologies communicate with each other or with other devices in and about a person. In some embodiments, a cell phone or other mobile device can operate as a central hub of the PAN to coordinate activities among the connected devices including the smart article. An example PAN system that can be leveraged for use with the disclosure subject matter are described in U.S. Pat. No. 10,667,212.

The ecosystem may include, in addition to the articles, other components. For example, the ecosystem may include devices (e.g., the central control station 102 of FIG. 1) with software applications supporting management of the articles. The software may include features for creating training data sets, capturing personalized images of a person's face, downloading data (e.g., machine learning code, images, etc.) to the articles, updating software instructions on the articles, and other management capabilities. Additional management capabilities include monitoring articles, inventorying assets of the articles (e.g., software version number, machine learning code version, digital image assets, etc.), logging events, generating alerts, generating reports, recovering a crashed device, securing assets possibly via cryptographic techniques, and/or other features. The software may be configured to execute on any suitable computing platform. The central control station may thus be, for example, a desktop computer, game console, smart phone, or other computing device. The software may be implemented on the mobile device 106 (e.g., smart phone, tablet, laptop computer, etc.).

The sensors 212, 412 of FIGS. 2 and 4 may include various sensors in various arrangements. The sensors may include piezoelectric strain or stress sensors that generate voltages based on a stress or strain. The sensors may be placed across a mask, face and/or other locations from which data may be taken. For example, stress sensors may be placed along strings (or bands) of a mask and/or across a surface of the mask and/or be used to connect the mask to the face. In an embodiment, the voltages are detected and converted to sensor data. This may be done by an analog-to-digital converter providing a one byte value (i.e., 0 to 255) or other digital forms; e.g., two bytes, three bytes, integers, floating point values, etc. Detecting a voltage based on stress represents a single sensed data modality. Other types of sensors may be included to detect addition data modalities. The sensors may include: thermal sensors to detect changes in emotion via temperature; galvanic sensors, capacitance sensors, resistance sensors, pressure sensors, and/or Hall Effect sensors to detect motion and/or position; airflow sensors to detect breath; accelerometers to detect head movement; gyroscopic sensors to detect head movement; audio sensors to detect spoken works or utterances; and/or other types of sensors.

The sensors may be placed in different arrangements that meet the needs of a predetermined article complexity and use of the article. For example, stretch or strain sensors may be placed vertically (i.e., a line parallel to the nose to chin line). FIG. 5A shows an example smart mask 500 including a single stretch sensor 502 in a similar arrangement. The sensor 502 is connected to a control circuit 504, which may include items in the smart mask visual communication system 402, such as the control module 404, the display 406, the memory 408, and the transceiver 410. The stretch sensor 502 may be used to detect movement of a person's jaw as the person speaks. As another example, three sensors may be placed about a mask; one placed half way between a right ear and right corner of a mouth, one placed in a middle of a face running from nose to chin, and another placed half way between a left ear and left corner of the mouth. Each signature of the sensors and/or a signature of the combined sensors aids in differentiating various jaw movements, such as speaking, emoting, grinding teeth, left or right shifting of the jaw, and other movements. Still further, a stress or strain sensor may be placed on a mask to be across a bridge of a nose to detect movement of a muscle around the nose. For example, if a person wrinkles the person's nose, possibly in disgust, the sensor would detect movements of muscles around the nose and might display a frown or other image representing the emotion of disgust. Air flow sensors can be used to detect inhaling or exhaling that might correspond to a gasp, cough, or other expressions that can translated to a corresponding or desirable image.

The sensors may also be directly coupled to a face of a person wearing a corresponding mask. Adhesive sensors may be placed beneath the mask, near the mask, and/or away from the mask. The sensors may be coupled to a control module via wired leads. For example, adhesive sensors may be placed near outer corners of eyes, near nostrils, near ears, and/or other locations. The sensors may detect small movement of muscles at these locations, which may correspond to emotions of the person, such as when a person smiles, but does not open the person's mouth. Often, the skin near the eyes wrinkle bringing life to the smile, which may be detected by such adhesive sensors. The sensors may include flexible sensors such as: bendable sensors; flexible touch force sensors; piezoelectric strip sensors; conductive rubber stretch sensors; stretch, splay, and compression sensors; adhesive thermal sensors; printed flexible sensors; Hall Effect sensors; etc. Example bendable sensors may be found at URL www.bendlabs.com/products, a flexible touch force sensor may be found at URL www.tekscan.com/products-solutions/electronics/flexiforce-oem-development-kit, a piezoelectric strip sensor may be found at URL www.omegapiezo.com/strip-actuators-bimorph-equivalent, a conductive rubber stretch sensor may be found at URL www.adafruit.com/product/519, stretch, splay, and compression sensors may be found at URL stretchsense.com/sensors, an adhesive thermal sensor may be found at URL starboard-medical.com/skin-sensors, printed, flexible sensors may be found at URL www.conductivetech.com/products/flexible-printed-circuitry, and Hall Effect sensors may be found at URL www.adafruit.com/product/158.

Figure 15:
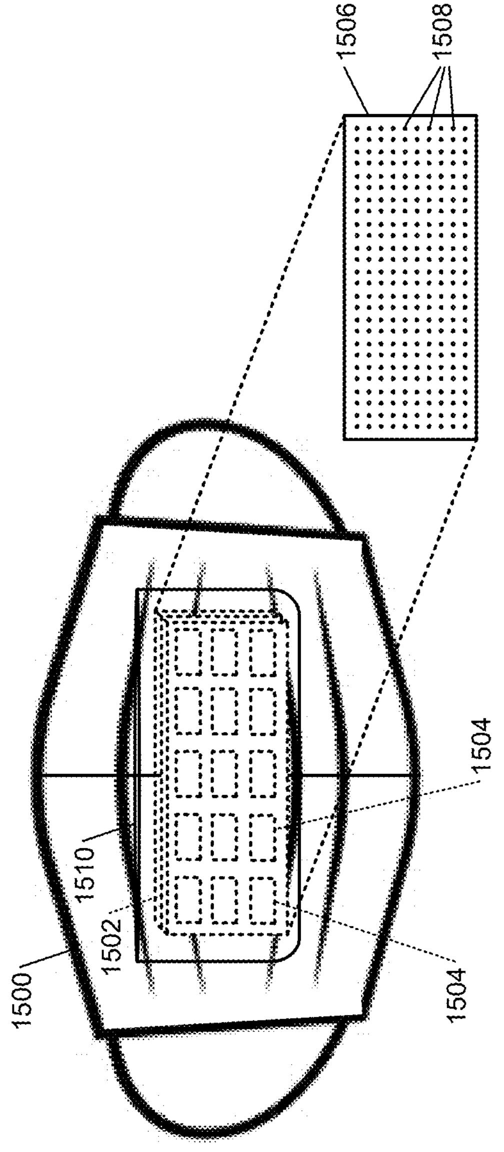
FIG. 15 is a back view of an example face mask including a filter with embedded sensors in accordance with the present disclosure.

The sensors may include multi-purpose sensors, such as sensors or sensor material offering antimicrobial features. For example, the sensors may include graphene-based nanomaterials having antibacterial features. For example, graphene-based nanomaterials have been found to offer antibacterial features (for example, see URL www.ncbi.nlm.nih.gov/pmc/articles/PMC6567318/. Example graphene-based sensors include: nanotube sensors (see URL www.ncbi.nlm.nih.gov/pmc/articles/PMC6523954/pdf/nanomaterials-09-00496.pdf), graphene health sensors (see URL www.frontiersin.org/articles/10.3389/fchem.2019.00399/full), graphene flex sensors (see URL www.cheaptubes.com/graphene-sensors), and printable graphene sensors (see URL www.nature.com/articles/s41528-019-0061-5). See URL www.sciencedirect.com/science/article/abs/pii/S0165993617300031 for an overview of graphene sensors. See URL www.directa-plus.com/for a source of graphene. An example of a graphene-based antibacterial mask is described at URL www.dezeen.com/2020/03/06/guardian-g-volt-face-mask-graphene-coronavirus-bacteria/. As an example, the materials of a mask and/or sensors of the mask may include graphene-based antibacterial materials. The mask may include graphene-based antibacterial material for filtering purposes. The mask may include an array of graphene-based antibacterial based sensors for detecting face movements. Similarly, copper also has antimicrobial properties and may also be used as a foundation for at least some of the sensors. As another example, a mask may include layers of material and/or sensors that are at least partially formed of copper for sensing and filtering purposes. Sensors based on silver would also be acceptable as it also has antimicrobial activity. An example of a mask including one or more sensors and one or more filters is shown in FIG. 15.

The displays (e.g., the displays 206, 406 of FIGS. 2 and 4) of the smart articles may be in various forms. In one embodiment, one or more of the smart articles may not include a display. The displays may include digital displays. In an example embodiment, a smart mask may be configured to render a visual digital image on the mask, where the display is flexible. The digital display of the mask includes a flexible display that can move or flex along with underlying facial movements. The displays may vary from low resolution displays to high resolution displays.

A low-resolution display may include a sufficient number of LEDs to permit forming a simulation of a mouth. For example, a set of red (or other colors) LEDs arranged in a 20×5 grid may be used to render or mimic just mouth movements where the LEDs may be sewn directly into the mask. The LEDs may be individually sewn into the mask or smart article or may be arranged on a flexible material layer of the mask and/or smart article. This "grid" may have a reduced number of LEDs by reducing the number of LEDs positioned near the corner of a mouth because the mouth corners would not move much during speech. The array of LEDs may be connected via flexible wires to permit movement and airflow. In various implementations, the grid of LEDs may be considered low-resolution if has a dots per inch (DPI) less than 70.

A high-resolution display may have sufficient resolution to display a full graphical image of a person's face and/or other images. In various implementations, the grid of LEDs may be considered high-resolution if has a dpi (dots per inch) greater than 70. The display may be a high definition (HD) or 4K (horizontal resolution of approximately 4,000 pixels, pixel density of 550 pixels per inch (PPI), 880 PPI, or even higher) display. The displays may include and/or be communicatively coupled to a processor, a power source (e.g., batteries, electrical cord, etc.), a graphics interface, and/or graphics processing unit (GPU). In other embodiments, the display 406 may be replaced with one or more screens, such as one or more green screens or projector screens on which images may be displayed as further described below. Further, display 406 can include a composite display including multiple smaller displays working in concert. Individually sewable LEDs can be found at URL www.adafruit.com/product/1755. A 160×32 display can be found at URL www.crystalfontz.com/product/cfal16032a0018pw-flexible-oled-display-160×32. An HD display can be found at URL newvisiondisplay.com/6-flexible-amoled/.

The mask 500 may include bands 505 that extend around, for example, a person's ears or back of the head. The bands 505 may be formed of elastic material and be stretchable or have a fixed length. The bands 505 may be replaced with ties and/or other attachment members. Similar bands are shown in FIGS. 5B-8.

Figure 5B:
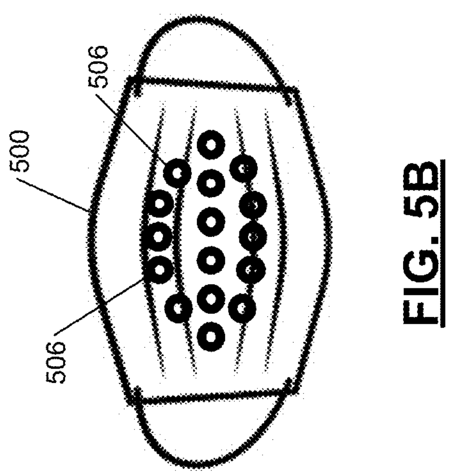
FIG. 5B is a front view of the smart mask of FIG. 5A including light emitting diodes (LEDs) in accordance with the present disclosure.
Figure 5D:
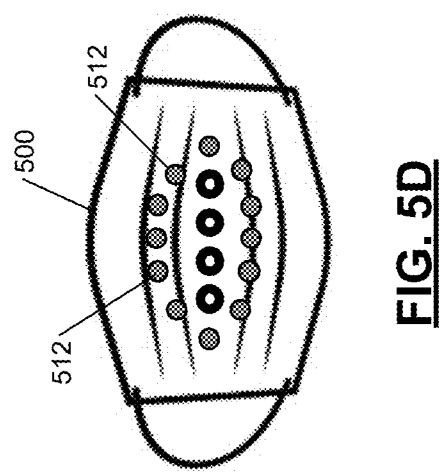
FIG. 5D is a front view of the smart mask of FIG. 5A illustrating certain ones of the LEDs in an ON state due to a person's mouth being in an open state.
Figure 5A:
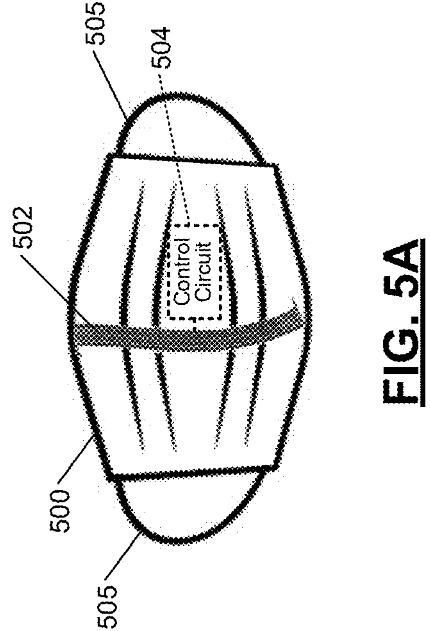
FIG. 5A is a back view of an example smart mask including a single stretch sensor in accordance with the present disclosure.
Figure 5C:
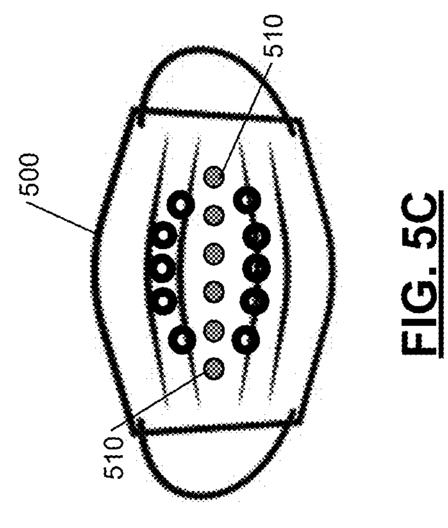
FIG. 5C is a front view of the smart mask of FIG. 5A illustrating certain ones of the LEDs in an ON state due to a person's mouth being in a closed state.

FIGS. 5B, 5C and 5D show the smart mask 500 including LEDs (a couple of which are designated 506). Although a particular arrangement of LEDs are shown including a particular number of LEDs, the LEDs may be in a different arrangement and include a different number of LEDs. In FIG. 5B, the smart mask is shown with the LEDs in an OFF state. In FIG. 5C, some of the LEDs (a couple of which are designated 510) are shown in an ON state due to a person's mouth being in a closed state where the ON LEDs form a line across the mouth region of the mask. In FIG. 5D, other ones of the LEDs (a couple of which are designated 512) are in an ON state due to a person's mouth being in an open state.

Figures 6, 7, 8:
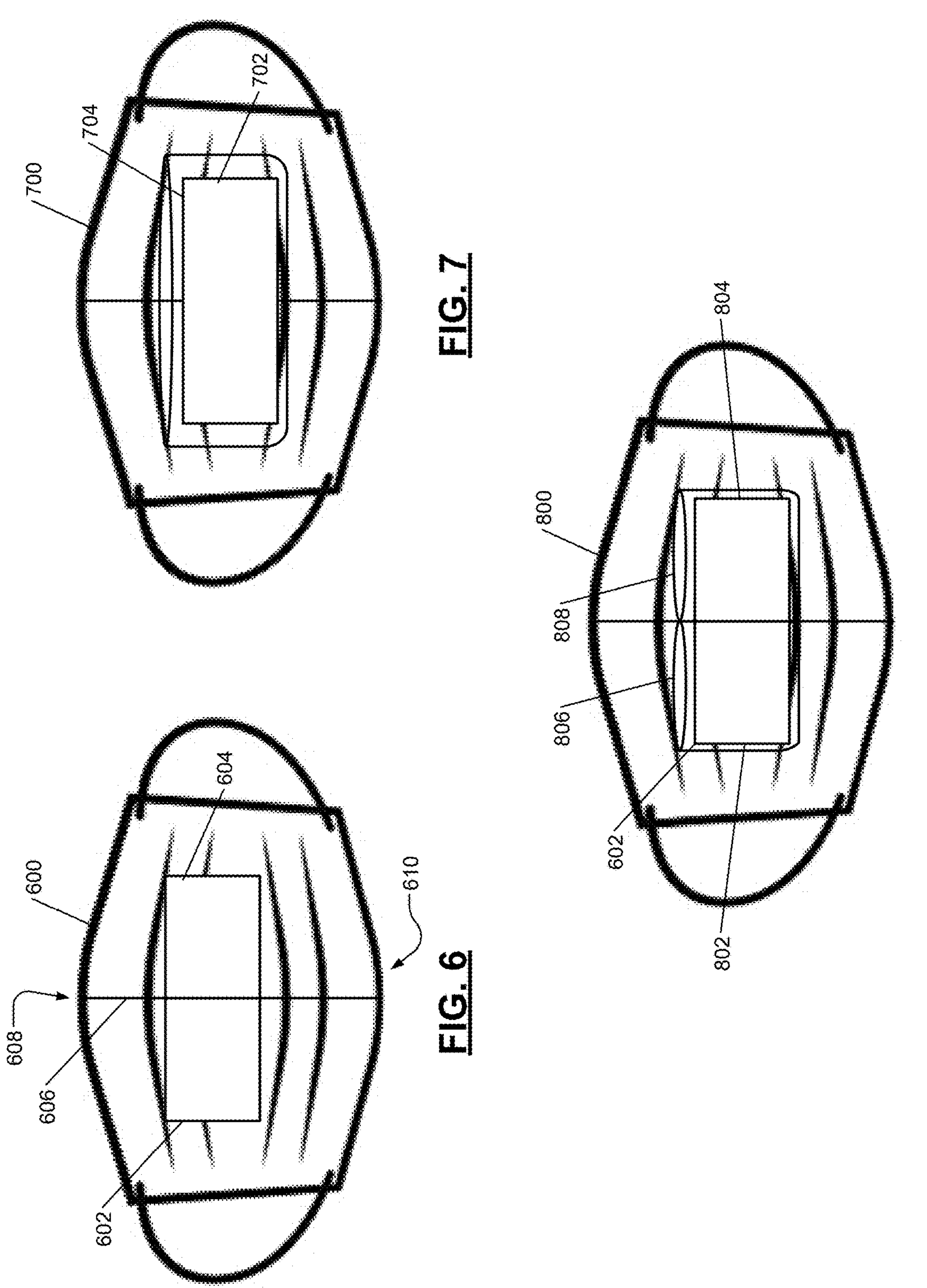
FIG. 6 is a front view of another example smart mask including multiple flexible displays in accordance with the present disclosure.
FIG. 7 is a front view of another example smart mask including a single flexible display in a transparent pocket in accordance with the present disclosure.
FIG. 8 is front view of another example smart mask including multiple flexible displays in transparent pockets in accordance with the present disclosure.

FIG. 6 shows a smart mask 600 including multiple flexible displays 602, 604. A mask may include more than one display, as shown. For example, the mask 600 may have a seam 606 joining a left and right portion of the mask and that extends from a nose area 608 to a chin area 610. In such cases, two or more flexible displays may be used to create a compound or composite display. For example, a single flexible display (display 602) may be positioned on the right side of a face and a second flexible display (display 604) may be positioned on the left side of the face, where the two displays mate at the seam 606.

A display may be integrated with a smart mask in several ways. In some embodiments, the display is integral to the smart mask, while in other embodiments, the display is part of a smart mask overlay that fits over an existing mask. Yet further, the displays may fit within transparent pockets to a mask system, which has advantages for modularity, upgrades, or repairs. Some examples of these embodiments are shown in FIGS. 7-15. Although not shown in these figures, the example, may include transceivers connected to the shown control modules for communicating with other devices as described herein. The transceivers may be attached to and/or integrated in any of the material layers shown.

FIG. 7 shows a smart mask 700 including a single flexible display 702 in a transparent pocket 704. FIG. 8 shows a smart mask 800 including multiple flexible displays 802, 804 in transparent pockets 806, 808.

Figure 9:
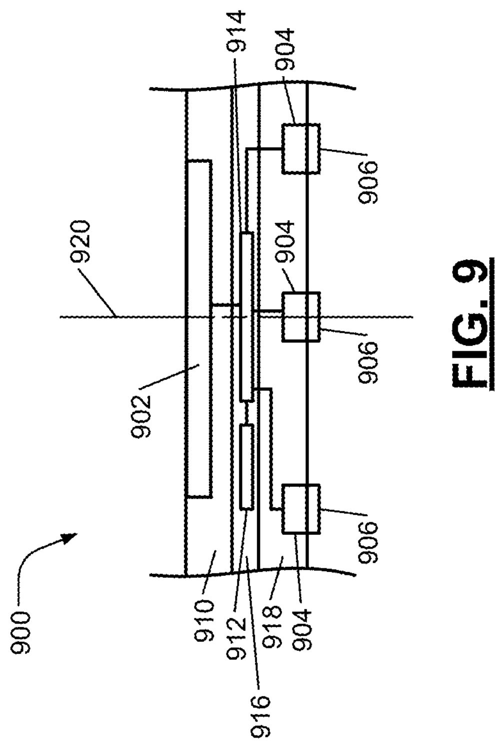
FIG. 9 is a side cross-sectional view of a portion of an example smart mask including an embedded display and sensors with skin adhering contacts in accordance with the present disclosure.

FIG. 9 shows a portion 900 of a smart mask including an embedded display 902 and sensors 904 with skin adhering contacts 906. The display 902 is embedded, connected to, and/or recessed in a first fabric (or material) layer 910. A power source 912 and a control module 914 are disposed in an intermediate fabric (or material) layer 916. The sensors 904 are disposed in another fabric (or material) layer 918. The contacts 906 are connected to the sensors 904 and may protrude outward from the fabric layer 918. A centerline 920 is shown. The control module 914 may be configured similarly as the control module 404 of FIG. 4.

Figure 10:
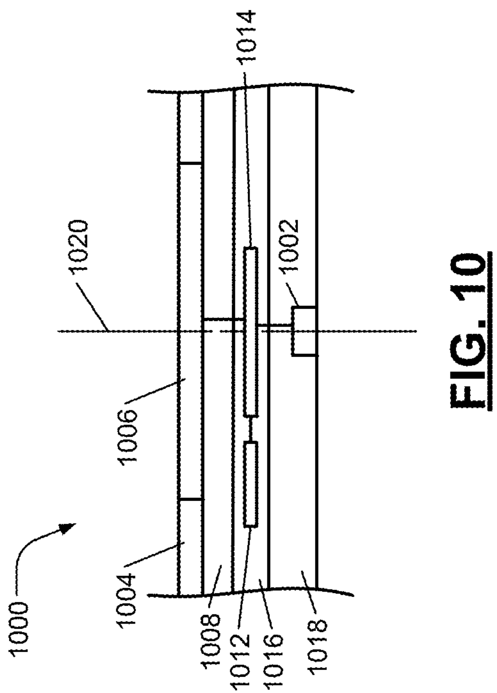
FIG. 10 is a side cross-sectional view of a portion of an example smart mask including a single stretch sensor and an overlay layer including a display in accordance with the present disclosure.

FIG. 10 shows a portion 1000 of a smart mask including a single stretch sensor 1002 and an overlay layer 1004 including a display 1006. The display 1006 is embedded, connected to, and/or recessed in the overlay layer 1004. The overlay layer 1004 may be disposed on a first intermediate fabric (or material) layer 1008. A power source 1012 and a control module 1014 are disposed in the first intermediate layer 1008 or in another intermediate fabric (or material) layer 1016, as shown. The sensor 1002 is disposed in another fabric (or material) layer 1018. A centerline 1020 is shown. The control module 1014 may be configured similarly as the control module 404 of FIG. 4.

Figure 11:
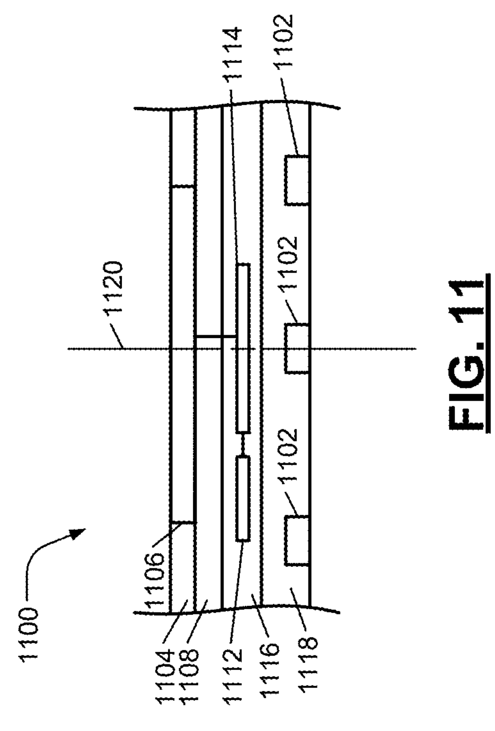
FIG. 11 is a side cross-sectional view of a portion of an example smart mask including multiple sensors and an overlay layer including a display in accordance with the present disclosure.
Figure 14:
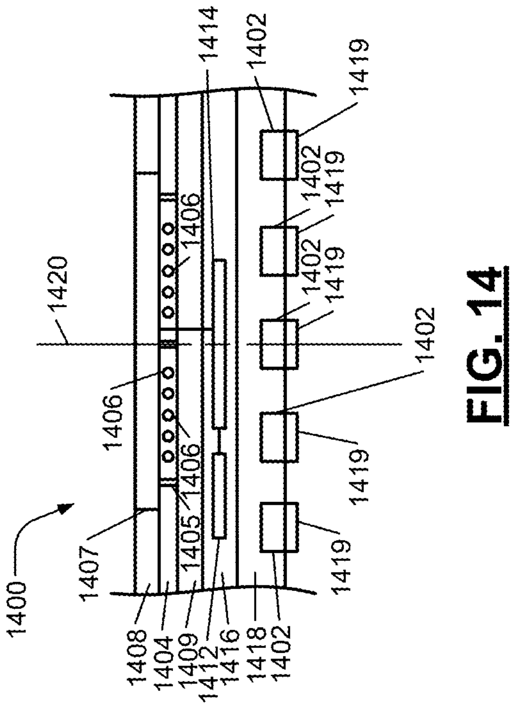
FIG. 14 is a side cross-sectional view of a portion of an example smart mask including multiple sensors and a cooling layer with channels for cooling a display in accordance with the present disclosure.

FIG. 11 shows a portion 1100 of a smart mask including multiple sensors 1102 and an overlay layer 1104 including a display 1106. The display 1106 is embedded, connected to, and/or recessed in the overlay layer 1104. The overlay layer 1104 may be disposed on a first intermediate fabric (or material) layer 1108. A power source 1112 and a control module 1114 are disposed in the first intermediate layer 1108 or in another intermediate fabric (or material) layer 1116. The sensors 1102 are disposed in another fabric (or material) layer 1118. A centerline 1120 is shown. The control module 1114 may be configured similarly as the control module 404 of FIG. 4.

Figure 12:
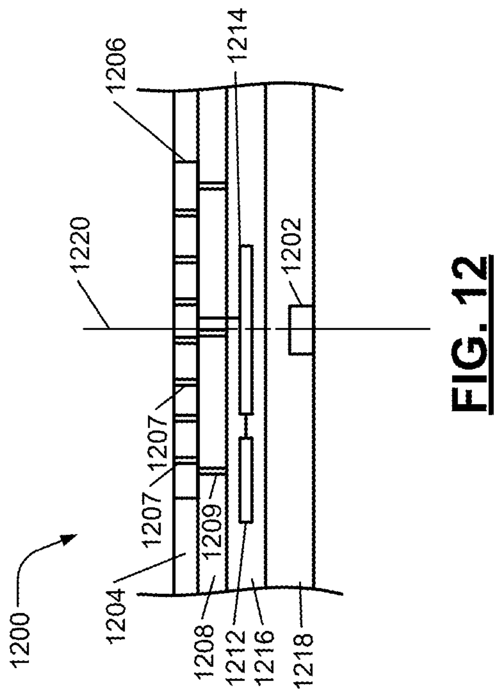
FIG. 12 is a side cross-sectional view of a portion of an example smart mask including an overlay layer, a sensor and a perforated display in accordance with the present disclosure.

FIG. 12 shows a portion 1200 of a smart mask including an overlay layer 1202, a sensor 1204 and a perforated display 1206. The display 1206 is embedded, connected to, and/or recessed in the overlay layer 1202 and includes perforations (or holes) 1207. The overlay layer 1202 may be disposed on a first intermediate layer 1208 including spacers 1209. A power source 1212 and a control module 1214 are disposed in a second intermediate (or fabric) layer 1216. The sensor 1204 is disposed in another fabric (or material) layer 1218. A centerline 1220 is shown. The control module 1214 may be configured similarly as the control module 404 of FIG. 4.

Figure 13:
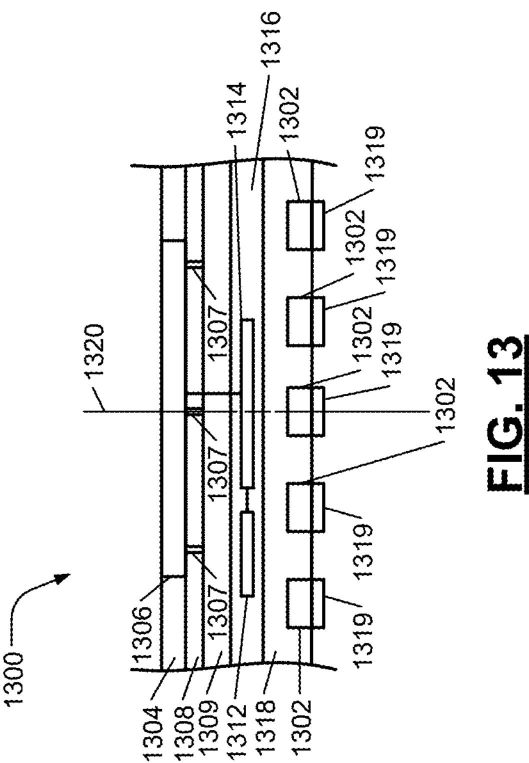
FIG. 13 is a side cross-sectional view of a portion of an example smart mask including multiple sensors and an overlay layer with a display spaced away from other layers in accordance with the present disclosure.

FIG. 13 shows a portion 1300 of a smart mask including multiple sensors 1302 and an overlay layer 1304 with a display 1306 spaced away from other layers via spacers 1307 and/or a spacing layer 1308. The display 1306 is embedded, connected to, and/or recessed in the overlay layer 1304. The overlay layer 1304 may be disposed on a first intermediate fabric (or material) layer 1309. A power source 1312 and a control module 1314 are disposed in the first intermediate layer 1309 or in another intermediate fabric (or material) layer 1316. The sensors 1302 are disposed in another fabric (or material) layer 1318 and may be connected to adhesive contacts 1319. A centerline 1320 is shown. The control module 1314 may be configured similarly as the control module 404 of FIG. 4.

The displays of a smart article may be positioned on risers to create an air gap, air plenums, and/or air channels through which air can flow freely under the displays. See, for example, FIG. 14, which shows a portion 1400 of a smart mask including multiple sensors 1402 and a cooling layer 1404 with spacers 1405 and channels 1406 for cooling a display 1407. The display 1407 is embedded, connected to, and/or recessed in an overlay layer 1408.

The cooling layer 1404 may be disposed on a first intermediate fabric (or material) layer 1409. A power source 1412 and a control module 1414 are disposed in the first intermediate layer 1409 or in another intermediate fabric (or material) layer 1416. The sensors 1402 are disposed in another fabric (or material) layer 1418 and may be connected to adhesive contacts 1419. A centerline 1420 is shown. The control module 1414 may be configured similarly as the control module 404 of FIG. 4.

FIG. 15 shows a face mask 1500 including a filter 1502 with embedded sensors 1504. The filter 1502 may include a stack of porous sheets of material (e.g., graphene, copper mesh, silver mesh, etc.) that permit airflow and have electrical properties that change and are measurable in real-time and operate as a sensor (e.g., stress, strain, etc. type sensor). Other configurations are also possible. For example, the sensors and filter material may be layered on one or more substrates that are porous or have air channels for airflow. An example porous substrate 1506 is shown having holes 1508. In the example shown, the filter 1502 is disposed in a pocket 1510.

In some embodiments, the flexible displays of the examples disclosed herein permit airflow through the corresponding masks. A display may have a mesh and/or a substrate with a set of holes that permits airflow through the display.

Although each of the masks of FIGS. 5A-15 include certain features, each of the masks may include any of the features shown in FIGS. 5A-15 and/or otherwise disclosed herein. Similarly, although each of the masks of FIGS. 5A-15 are shown as not including certain features that are shown in other ones of FIGS. 5A-15 and/or disclosed herein, each of the masks may include any of the features shown in FIGS. 5A-15 and/or disclosed herein.

From a high-level perspective, a mask controller receives and/or otherwise obtains sensor inputs and converts the inputs to output values representing facial positions or other types of classifications. The output values are then used to determine what images are to be rendered on the display of the mask. More specifically and in some embodiments, the sensed values are compiled as an input vector and fed into (or provided as inputs to) one or more functions that convert the sensed values to facial landmark positions or classes. The landmark positions may be used to generate corresponding rendered images of the person's face and facial features at positions corresponding to landmark positions. Example landmark positions are shown in FIGS. 16B-D.

FIG. 16A shows a mouth of a person in a silent and neutral position. FIG. 16B shows the mouth of FIG. 16A with overlaid landmarks and an origin. The origin is a reference point, which may be centrally located in an image or located elsewhere. FIG. 16C shows the mouth with the overlaid landmarks moved to different locations associated with mouth movement (or an open mouth position) and relative to the origin. FIG. 16D illustrates positioning of landmarks relative to the origin.

For illustrative purposes, consider a scenario where a mask includes four sensors that generate values between 0 and 255. At any given sensed time (e.g., periodically, when triggered by activation criteria, every millisecond (ms), every 5 ms, etc.), the control module of the mask may generate an input vector of four bytes, where each byte represents a value of a corresponding sensor. Four facial landmarks may be implemented: two landmarks over respective corners of the mouth, one over the upper lip, and another over the low lip of the person. The four byte sensor input vector is mapped and converted to a set of positions for the four landmarks (e.g., (x, y) coordinates for each landmark, a single relative distance value from an origin, and/or other position value, etc.). In this example, the mapping function may not be one-to-one (i.e., one sensor value corresponds to a single face feature). Rather, the four sensor inputs may be indices of a 4D space, which yields a corresponding landmark position. The 4D space can subdivided into regions where reach region represents mouth positions or landmark positions. This may be referred to as a brute force, look-up approach. The mapping space may be reduced by using principle component analysis to achieve a target, more memory efficient, output mapping.

In this example, the mapping function may operate as a classifier implementing a support vector machine (SVM) algorithm, a k nearest neighbor (kNN) search algorithm, a random forest algorithm, etc., where the landmark positions represent classes. In such an approach, the identified classes may correspond to specific images that should be displayed. Thus, the mapping function or functions for the four landmarks may be at least similar to the following: Rc(S), Lc(S), UL(S), LL(S) where Rc==right corner of mouth; Lc==left corner of mouth; UL==upper lip position of mouth; LL==lower lip position of mouth. S is an input vector having sensor values. One should keep in mind that these mapping functions represent software instructions and may thus employ various executable instructions stored in memory. As mentioned previously, the mapping functions may leverage an implementation of a classification algorithm. However, the mapping functions may also be implemented as a lookup table as alluded to above.

AI Training

In one embodiment, artificial intelligence (AI) training is implemented. This may be done to train any of the control modules referred to herein including the modules 110, 204, 302, 404 of FIGS. 1-4. The AI training may include any of the below described training features and operations including operations similar to that performed during the methods of FIGS. 17-19. The operations of FIGS. 17-19 may be performed subsequent to and/or while AI training is being performed.

According to an example embodiment, an AI visual data training set may be created by recording a video of a person reading a preset text that causes the person's face, without wearing a mask, to make known movements as matched with spoken words and/or with known expressions (phonemes, smile, frown, smirk, emotes, utterances, etc.) This training set provides for capturing images of the person's face for later rendering on one of the smart masks and/or articles disclosed herein. An AI sensor data training set may be created by having a person put on a digital display mask and/or sensors and repeating the same training process as described above while recording sensor data, which may be received at and/or by one or more of the smart masks and/or articles disclosed herein. This training data set may be compiled at a same time as the image training data set. The training data provides for matching sensor data to the corresponding spoken words and to the corresponding images of the person's face at various positions and/or during movements.

A neural network implemented by one of the control modules is trained based on the training data set such that sensor data input is converted to a visual representation of the person's face. As the person speaks with the smart mask on, the AI senses the real-time sensor data, which may include audio (e.g., voice) data or other data modalities. The mask uses the real-time sensor data, which may include facial movement (or physical face) data and/or voice data as input to the trained neural network, which outputs an identifier representing an image of the person's face corresponding to the neural network inputs.

While one of the preceding examples focuses on converting the sensor inputs to four facial landmarks, the mapping function implemented by one of the control modules may operate as an intermediary between the sensor inputs and the displayed images. Thus, the mapping function may simply generate an image identifier (ID) corresponding to an image to be displayed. For example, the image ID may be a file name of an image stored in the memory (e.g., a file system) of the control module of the mask.

As another example, 44 images may be generated to be displayed, each image corresponds to a mouth arrangement for 44 known phonemes in English. The mapping function may generate an image ID of 37 indicating that image 37.png should be rendered. The approach of converting the sensor inputs to an image ID is considered advantageous because it allows the user to swap out the images and replace them with any other images (in some embodiments, as long as the images have file names in the same ID space). Thus, a control module may replace facial images of a first person with images from another person's face (e.g., a celebrity, a cartoon character, etc.) based on user input. In another embodiment, the images do not correspond to a face or phoneme mouth position, but are images of something else, such as: a tree, a car, a dog, a pet, a logo, a set of emoticons, etc. It should be appreciated that such embodiments might be best served as novelties. While it is contemplated that the training software might map to known phonemes or emotions, it is also contemplated that a user could create custom configurations where they map a sensor signature to a custom image. For example, a user might map non-phoneme utterances (e.g., "Ugh", "Arg", "Hmmm", raspberry sound, etc.) or other facial movements to a desired image. Perhaps "Arg" might be mapped to an image of pirate, or an emoticon expressing anger.

In more complex implementations the number of sensors may vary and the number of face positions and/or landmarks may vary. The number of sensor inputs may not correspond to the number of face positions or landmarks. While some embodiments include one sensor state mapping to one output image, other embodiments are more complex and include generating more than one output image. Thus, the mapping function may take on a full spectrum of mappings: one-to-one, one-to-many, many-to-many, etc.

While the disclosure to this point may be directed to a personalized or customized mapping function, a mapping function may operate based on a default configuration or a default setting. The default configuration may be based on a generic mapping of sensor values to a set of generic mouth arrangements corresponding to spoken phonemes, where the arrangements may correspond to landmarks that are tracked. Further the default configuration may be compiled based on AI or machine learning training data sets compiled from many individuals. Example mouth arrangements and positions may be mapped to corresponding phonemes. See URL www.rose-medical.com/mouth-positions.html.

Another example of a more complex embodiment includes implementations executing code of the mapping function corresponding to a trained neural network (NN) that accepts the sensor input vector and outputs desires mouth positions, landmark positions, image IDs, and/or other information used to render a desired corresponding image. In NN embodiments, one or more training data sets are compiled based on sensor values and corresponding to spoken phonemes, emoted facial positions, custom sensor signatures, and/or other facial arrangements. Further, in some embodiments, the training data set may be compiled on a person-by-person basis to ensure the training data is highly personalized. In other embodiments, as referenced above, the training data set may be built from hundreds, thousands, or more users thus representing a default or base configuration. The training data set could be created via a crowd-sourced effort where data is collected and integrated into the software for the smart article ecosystem. An example technique that could be adapted for use in creating crowd-sourced face movement to image training data sets are described in U.S. Pat. No. 10,147,038. Data from the specific user may then be captured followed by the NN trained on the default data set being refined based on the user's data set. In yet another embodiment, the training data set may be the default data set without modification.

A mask management software application may be executed by one or more of the control modules to create a training data set. The mask management software may be executed to observe a person's face and/or sounds uttered by the person via a camera and/or microphone. Landmarks on the person's face are observed while the person's face proceeds through known positions. Corresponding images, face positions, landmark positions, and/or facial features are captured and recorded. Facial features may be observed using face recognition capabilities and face feature detection capabilities. Facial features can be observed based on one or more available software packages, such as OpenCV (see URL www.opencv.org), which offers both face recognition capabilities and face feature detection capability. For example, the application may use one or more implementations of feature detection algorithms to track the landmarks of a person's face. Example algorithms include Canny edge detection, edge vectors (see U.S. Pat. No. 9,412,176), scale-invariant feature transform (SIFT; see U.S. Pat. No. 6,711,293), histogram of oriented gradients (HoG), speeded up robust features (SURF), or others. Further, the algorithms may track specific landmarks such as the 68 landmarks as part of an intelligent behavior understanding group (iBUG) 300-W dataset (see URL ibug.doc.ic.ac.uk/resources/facial-point-annotations/).

Returning to compiling the training data set, each of the facial landmarks may be tracked by the management application as a person enacts a known script, where the script corresponds to known facial positions. The script may include a set of words that correspond to phonemes (see URL en.wikipedia.org/wiki/Phoneme), which have known positions. Further the script may include emotional actions such as smile with mouth open, smile with mouth closed, frown, laugh, wince, emote fear, emote surprise, etc. Naturally, every language has a respective set of phenomes. For example, English is considered to have 13 to 21 vowel phonemes and about 22 to 26 consonant phonemes; around 44 total. Thus, in English, the person may recite a script that has the person utter each of the phonemes, preferably multiple times and in different orders to ensure capturing various aspects of the persons face as the portions of the face move (e.g., still images of mouth, audio of voice, video of mouth, transitions from one phoneme to another, etc.). Thus, the software compiles a mapping of the phonemes to landmarks as well as a mapping of the phonemes to actual images of the persons face at the moment or the process of uttering the phonemes. A list of words that correspond to 44 phonemes in English are known and may be found at URL www.dyslexia-reading-well.com/44-phonemes-in-english.html. The words from this list may be used to construct a script to be read by the user. In some embodiments, the user can create custom scripts and custom images to fit their own needs.

One advantage of having the person read multiple scripts having different orders of phonemes is the management application may identify transitions of facial landmarks from one phoneme to another and thereby capture video of the transitions. Videos of such transitions are used for improved rendering fidelity and performance when the person wears the mask and speaks. The video transitions or a digitally constructed transition (e.g., a 3D digital model of a face, a 2D animation model, etc.) may be rendered in real-time on the display of the smart mask (or article).

As the control module executing the management application observes a person, the control module may display the script to prompt the person to say the specific words in the script at specific times. While observing the person, the software may employ speech recognition to map the landmark tracking to the phonemes. Further, by presenting the prompt to the person at the same time as employing the speech recognition, the software is able to better handle accents.

FIGS. 16A-D (collectively FIG. 16) provide a simple illustration of mapping landmarks of a person's mouth to a phoneme (see URL www.rose-medical.com/mouth-positions.html). As shown, the mouth may be initially at rest and thus in a silent or neutral positon. This image may be displayed on the mask when the sensors lack any sensed movement. While at rest or at a neutral position, the software executes one or more implementations of facial detection algorithms (e.g., OpenCV, etc.) to identify landmarks in the image data. In the example shown, a small number of landmarks are shown relative to an origin point. The origin is shown as a location near the center of the lips, but may be any practical location or might not be necessary in some implementations. Further, in some embodiments, the origin corresponds to the center of the mask's display or a position relative to the center of the mask's display.

The origin point may be found based on the landmarks or other image features. For example, a center point of the lips and/or a fixed distance from the nose. Such positions may be calculated by triangulation, calculating a centroid of landmarks, and/or other suitable techniques. As a person speaks the phonemes, the landmarks move in space. In the example shown, the mouth is in a position to articulate the "k" sound in "kit". The facial feature detection algorithm tracks the movement of the landmarks and calculates the new positions in real-time or near real-time relative to the origin or relative to the landmarks' previous positions. Thus, the software is executed to generate data representing landmark positions and movement during phoneme utterances.

In some embodiments, the data is a set coordinate values. For example, the coordinates could be (X, Y) coordinates relative to the origin, difference in X and Y relative to origin, difference in X and Y relative to previously positions, or other measurements. While the origin is shown in the middle of the lips, the origin may be placed at any position that is able to be reliably determined. The origin may be used to as a reference point for rendering the mouth or lip images on the mask in a consistent manner. Such rendering may be achieved through a graphics rendering engine that moves a 2D or 3D model of a mouth relative to the origin with textures from the person. However, an origin is not necessary in embodiments that simply display static images of a person's mouth that correspond to the sensed positions, sensed utterances, sensed emotes, or according to other sensor signatures.

Once the management software completes observation of the person reading a script, the software has a data set mapping the phonemes to facial landmarks and/or facial image features. This mapping may also include audio data of uttered phonemes in the person's voice that also map the facial landmarks or image features.

At this point, the software maps phonemes or utterances to a visual rendering. Further data would also be useful to create a mapping of mask sensor data (e.g., facial movement, audio, etc.) to the facial landmarks or image features. A mask can obscure a person's face. Sensors are thus used to detect actual movement of the person's face beneath the mask to determine what images or renderings to display via the display of the mask.

The management software, the same application or another data collection application, running on a data collection device (e.g., a personal computer, a cell phone, the mobile device of FIG. 3, etc.) creates a data set representing a mapping of the sensor data to the phonemes and/or facial landmarks as the person enacts or reads the script. The data set may be created by having the user wear the sensors associated with the mask (e.g., the mask itself if the sensors are embedded or just the sensors if the sensors are not embedded at the same time as reading the script to capture image data). The person then may repeat the script. In embodiments where the sensors are separate from the mask and do not obscure the face, sensor data collection process can be done at the same time as the image data collection process. For the sake of discussion, assume the sensors are integrated into the mask. The person again enacts or reads the script by following prompts generated through execution of the software as the script is displayed to the user via a display screen. The software may include code for displaying the script. The software is executed to collect corresponding sensor information occurring at the same time as the person speaks the phonemes or emotes. The resulting data then includes a collection of sensor data vectors (e.g., a data set having one or more sensor data feeds) that map to corresponding phonemes, landmarks, and facial image data. This process may be repeated any number of times to collect larger data sets by which the system learns. Further, the training data may include data from dozens, hundreds, thousands or more users.

The sensor data set may take on many different forms depending on the desired complexity. In low complexity embodiments, the sensor data may include static values obtained from the sensors when the management software determines the person's face is in a proper position. For example, the software might display the word "kit" for the person to read. The software may identify two main phonemes "k" and "t" for the sake of discussion. Leveraging audio data, the software may determine the sensor data at the time the "k" sound was uttered and the sensor data at the time the "t" sound was uttered. Thus, in this simple example, two sensor data sets would be compiled: one for "k" and one for "t". More specifically, if there are four strain sensors having values between 0 and 255, the "k" sound set would have four bytes specific to the "k" sound and four byes specific "t". In some phoneme scenarios, the mouth positions may be very similar and the sensor data may not be conclusive as to the phoneme being uttered. In moderately complex embodiments, other sensor modalities may come into play. For example, an audio transducer may be included that detects the sound of a person's voice. Using another sensor data modality may offer advantages including differentiating among similar sensor signatures. In yet more complex embodiments, the senor data may include time-series data representing how the sensor data changes with time. Thus, the time-series sensor data may be mapped directly to the time series image data of the person's face (e.g., video, etc.).

The sensor data may include time series data. Some embodiments may leverage values derived from the sensor data in lieu of or in addition to the sensor data. For example, derived values may include higher order time derivatives of the sensor data. Using derived values, which may also be time series, aids by mapping sensed mouth movements to movement of facial landmarks in the image data and further aids in identifying transitions from one phoneme to another. Both the sensor data and the first time derivative of the sensors may be used as an input. In this case, a vector may have a time value, sensor values, and time derivatives of the sensor data. Thus, for a four-sensor system, the input vector would have nine values. If a transition cannot be detected in real-time, the mask control can display a default transition image such as a mouth at rest, then proceed to the next image as indicated by the sensor data.

Returning to the use of machine learning techniques, one should appreciate that the disclosed approach could use classifier techniques, regression techniques and/or other machine learning techniques to convert the sensor data to renderable images. Classifiers (e.g., SVM, kNN, NNs, etc.) may be trained based on the sensor training data sets with respect to a set of images corresponding to the phonemes. Thus, the classifier accepts the sensor input and may generate at least one image, which is then displayed on the mask's display. In this embodiment, the set of images may include just static images for the various phonemes, emotes, or other mouth positions, where the static images represent the classes for the classifier. Further, each static image can be displayed for a desired amount of time before displaying a next image (e.g., display for 0.2 seconds, display until a next image is found, etc.). While these examples are presented with respect to classes represented by images, the classes may also be defined by positions of facial landmarks, which may then be used to generate a graphical 2D rendering of the person's mouth possibly based on a digital model of a mouth or face.

It is also possible to combine multiple classifiers together, an SVM plus an artificial neural network (ANN) for example, where the results of multiple classifiers represent a "vote" for an image to be displayed. Regression techniques offer greater fidelity when displaying images because regression techniques generate interpolations between or among various positions. Rather than generating a classification, a regression technique generates predictive or forecasted values representing positions of the mouth as a function of the sensor data. Such techniques convert sensor time-series data to corresponding mouth positions or facial landmark positions or movements as time-series data. There are many types of machine learning regression models (e.g., linear regression, ridge regression, least absolute shrinkage and selection operator (LASSO) regression, elastic net regression, neural networks, etc.), from which to choose. The choice of one or more regression models depends on the desired complexity of the resulting displayed images and the number of sensors in the system.

As discussed above, the sensor data may be mapped to facial landmarks, especially mouth landmarks. For example, the executed software may track such landmarks. For example, computing packages, including dlib or OpenCV, offer the ability to track such landmarks. As referenced further above, the facial landmarks may include 68 landmarks, where 20 represents the mouth (see URL ibug.doc.ic.ac.uk/resources/facial-point-annotations/). The outputs of the sensors may be mapped to the corresponding positions and/or movement of the landmarks. As another example, four sensors and 20 landmarks may be monitored.

The 20 landmarks may each have an (x,y) coordinate, which may be tracked relative to an origin based on the phonemes or emotes as sensed by the sensors. Assuming for the sake of discussion, the outputs of the four sensors are mapped to the 20 landmarks, such that the input vector to the neural network is four bytes. The output of the neural network may include 20 (x,y) value pairs corresponding to the predicted positions of the 20 mouth landmarks in a suitable coordinate system for display, where the prediction positions may then be used to create a rendering of the person's mouth on the mask's display. Multiple different architectures may be implemented for a neural network that provides these features, all of which are considered to fall within the scope of this disclosure. The complexity of the neural network may vary depending on the fidelity of the output, cost to build, and/or other factors.

The NNs may leverage a recurrent neural network (RNN) that receives four inputs and generates 20 output values. In general, NNs that have reduced memory footprints and quickly generate a result in real-time reduce the cost to create the mask. For example, in the instant example, the NN may use an input layer having four nodes, one or more fully connected hidden layers, and an output layer having 20 to 40 nodes depending on the desired output, where the output layers provide values that may be mapped to facial landmarks. For such a use case, a convolutional neural network may prove useful as it would have a smaller memory foot print. The type of model used to map the sensor outputs to the displayed outputs may be varied to fit a particular need. Thus, the model used may be a fully connected neural network, convolutional neural network, a transformer, a classifier, and/or other types of models.

As another example, a basic classifier of one of the control modules disclosed herein may be used for a mask with a single stretch sensor (an example of which shown in FIG. 5A) stretching across the mask from nose to jaw, which fits a face snuggly. The display of the mask may include a set of sewn in LEDs arranged to mimic an open and closed mouth of the face. This mask is an example of a low-end, low cost embodiment. The sensor has a resistance depending on a degree of stretch (e.g., high resistance when relaxed, low resistance when stretched, etc.). As the sensor stretches during mouth movement, the control module of the mask may detect changes in the resistance (e.g., via a voltage change, via current change, etc.). The control module may determine if the mouth is open or closed. When the control module determines the mouth is closed via a sensed resistance value or range, the control module turns the LEDs on in the closed arrangement. When the control module determines the mouth is opened via a different resistance value or range, the control module turns off the LEDs in the closed arrangement and turns on the LEDs in the open arrangement. The purpose of providing this simple example is to illustrate that the model used to determine mouth position may be a very basic classifier where sensor input values are compared to thresholds or a single criterion to determine a class (i.e., open or closed) and display a corresponding result. Higher end masks may employ more sophisticated classifiers and/or regression models as disclosed herein having dozens, 100s, or more classes.

Figure 17:
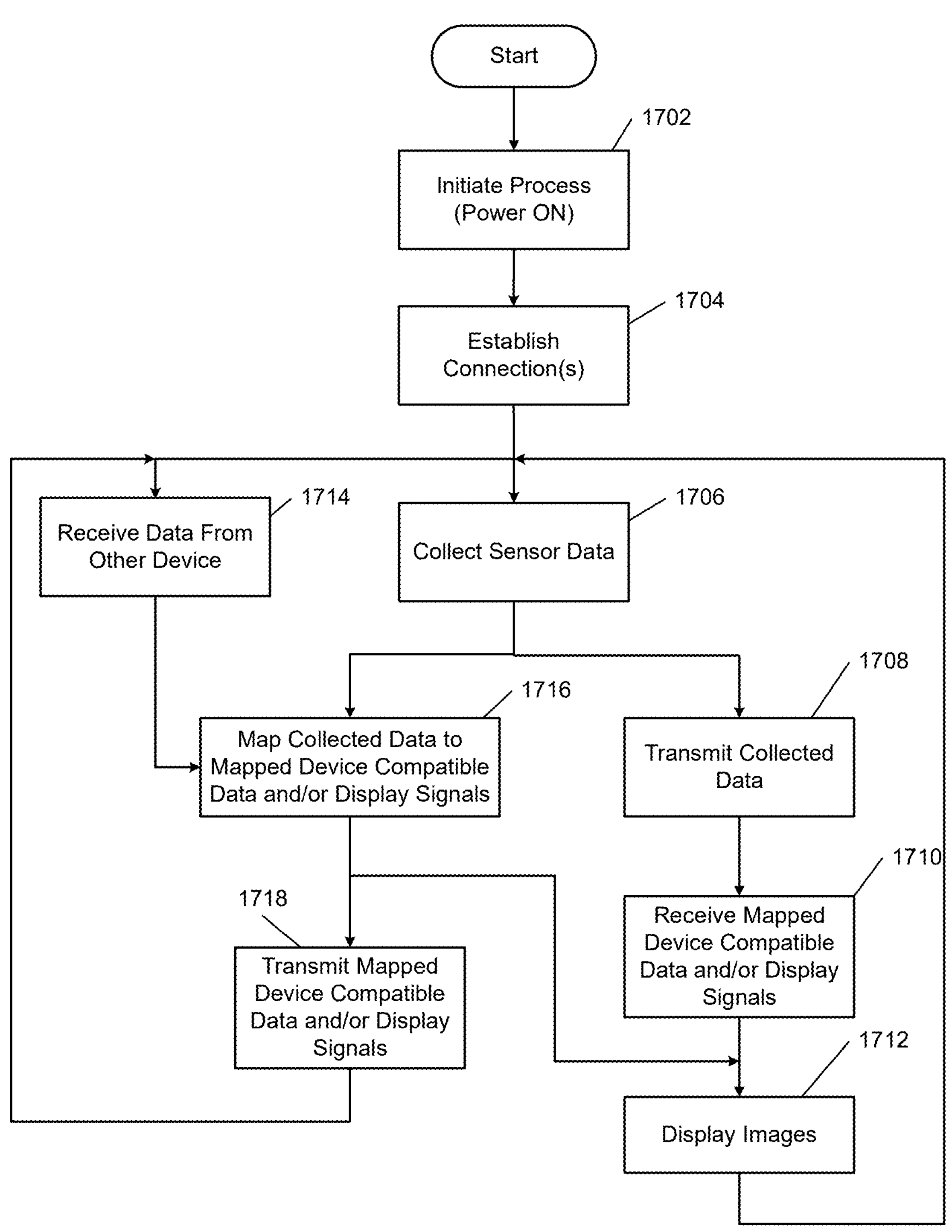
FIG. 17 illustrates an example article operation method according to the present disclosure.
Figure 18:
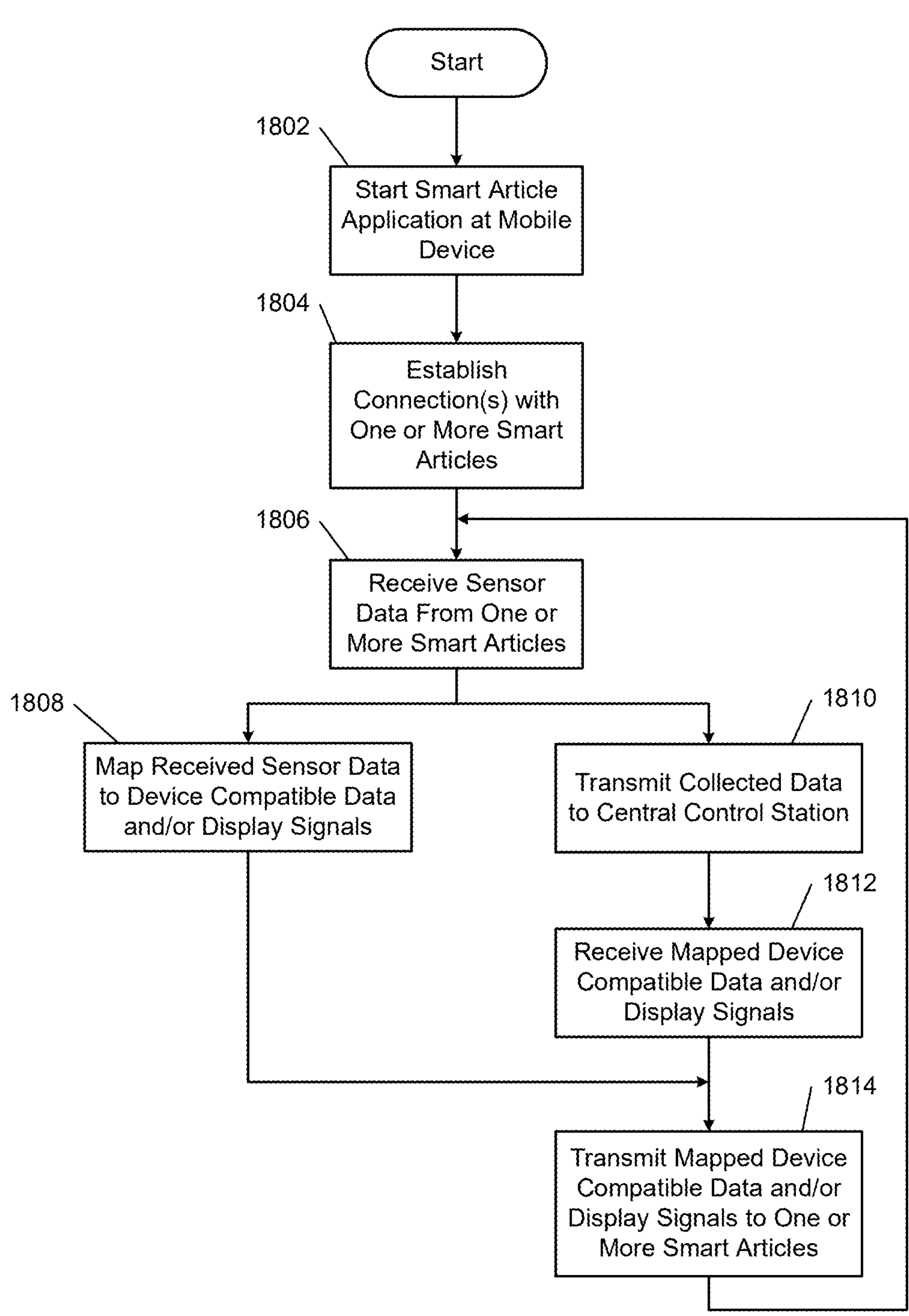
FIG. 18 illustrates an example mobile device operation method according to the present disclosure.
Figure 19:
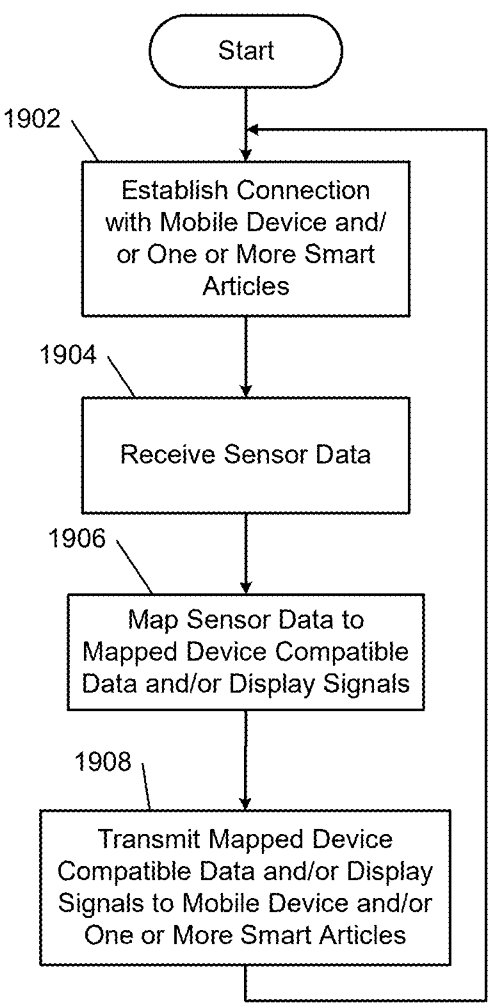
FIG. 19 illustrates an example central control station operation method according to the present disclosure.

The systems and devices disclosed herein may be operated using numerous methods, example methods are illustrated in FIGS. 17-19. The following methods may each include an AI and/or neural network learning process as described herein, which may be implemented prior to and/or during any of the following methods.

In FIG. 17, an example article operation method is shown. Although the following methods are shown as separate methods, the methods and/or operations may be combined and performed as a single method. Although the following operations are primarily described with respect to the implementations of FIGS. 1-4, the operations may be easily modified to apply to other implementations of the present disclosure. Although FIG. 17 is primarily described with respect to the smart article 400 of FIG. 4, the operations are applicable to the smart mask 200 of FIG. 2. The operations may be iteratively performed.

The method of FIG. 17 begins at 1702, where the article control module 404 may be powered ON and initiate facial movement tracking software stored in the memory 408 and executed by the article control module 404.

At 1704, the transceiver 410 may establish a connection with one or more devices, such as the central control station 102 and/or the mobile device 300. At 1706, the article control module 404 may collect sensor data from the sensors 412. At 1708, the article control module 404 may transmit the collected sensor data to the central control station 102 and/or the mobile device 300.

At 1710, the article control module 404 may receive mapped device compatible data and/or display signals from the central control station 102 and/or the mobile device 300 based on the collected sensor data. At 1712, the article control module 404 may convert the mapped device compatible data to display signals and display images based on the mapped device compatible data or display images based on the received display signals. At 1714, the article control module 404 may receive sensor data from one or more other smart articles. At 1716, the mapping module 415 may map the sensor data collected from the sensors 412 and/or from the other one or more smart articles to mapped device compatible data and/or display signals.

At 1718, the article control module 404 may transmit the mapped device compatible data and/or display signals to the other one or more smart articles. Operation 1712 may be performed subsequent to operation 1716 and display the mapped device compatible data and/or the display signals generated at 1716. The method may end subsequent to operation 1712 or may return to operation 1706 as shown.

FIG. 18 shows an example mobile device operation method. The method begins at 1802, where the smart article application 310 is started. This may be based on an input received from a user of the mobile device 300 or other sensed triggering event.

At 1804, the mobile device control module 302 via the transceiver 308 establishes connection(s) with one or more smart articles (e.g., the smart articles 200 and 400) and may also establish a connection with the central control station 102. At 1806, the mobile device control module 302 may receive sensor data from the one or more smart articles.

At 1808, the mapping module 311 may map the received sensor data to device compatible data and/or display signals. At 1810, the mobile device control module 302 may transmit the collected data to the central control station 102.

At 1812, the mobile device control module 302 may receive mapped device compatible data and/or display signals from the central control station based on the transmitted collected data. At 1814, the mobile device control module 302 may transmit the mapped device compatible data and/or display signals generated and/or received to the one or more smart articles. The method may end subsequent to operation 1814 or may return to operation 1806 as shown.

FIG. 19 shows an example central control station operation method. The method begins at 1902, where the central control module 110 of the central control station 102 may establish connection(s) with the mobile device 300 and/or one or more of the smart articles (e.g., the smart articles 200 and 400).

At 1904, the transceiver 112 may receive sensor data from the sensors 116, the mobile device 300 and/or the one or more smart articles. At 1906, the central control module 110 may map the sensor data to mapped device compatible data and/or display signals. At 1908, the central control module 110 may transmit the mapped device compatible data and/or display signals to the mobile device 300 and/or the one or more smart articles. The method may end subsequent to operation 1908 or may return to operation 1902 as shown.

The above-described operations of FIGS. 17-19 are meant to be illustrative examples. The operations may be performed sequentially, synchronously, simultaneously, continuously, during overlapping time periods or in a different order depending upon the application. Also, any of the operations may not be performed or skipped depending on the implementation and/or sequence of events. Additional operations may also be performed as disclosed herein.

The following examples include additional details and variations of the above-described embodiments. The operations described below may be implemented by the smart articles disclosed herein.

Sensors may be arranged around a mask, face, mouth, or head of a mask wearer in various patterns and in various configurations. For example, stretch sensors may be placed across the mask diagonally from a lower left jaw to an upper right cheek and vice versa. Sensors may be integrated into a mask, where the mask is properly fitted to a person's face to ensure optimal sensor performance. A mask system may have various capabilities. Low-cost masks may have a few sensors. High-cost, high performance masks may have a larger number of high fidelity sensors. Additionally, sensors may be affixed to various articles around a person including glasses, hats, scarves, shirt collars, and/or other articles and/or portions thereof. For example, image sensors may be disposed near eyes to observe pupil dilation to determine emotional response, which may then be used to determine which emotion to render on a display of a smart article or may be used to render a corresponding emotion.

As sensor complexity may vary, display functionality may also vary. At one end of a spectrum, the displayed images on the mask do not necessarily correspond to the actual phonemes, emotions, or other expressions. This end of the spectrum may be considered as a novelty for entertainment purposes, where the displayed images may be considered comical, entertaining, and/or just fun. At the other end of the spectrum, the precision of the displayed images on the mask match closely to actual expressions of the wearer. The high precision version of the mask likely costs more, but is considered advantageous where communication among individuals is critical. Example use cases include interactions with patients at points of care, business meetings, and/or other similar situations. An intermediary point on the spectrum between the low-end and high-end may be leveraged by retail sales, where some precision is necessary to convey interest in another person, but is not critical.

While some embodiments as described may be based on an assumption that displayed features correspond to sensed mouth positions, there is no requirement that the displayed images are images of a mouth. For example, the images displayed may include sign language, text in a native language of the speaker wearing the smart mask, translated text in another language, emoticons, and/or other images. Additionally, the displayed images may not be displayed on a mask, but may be displayed on other articles, such as a hat, shirt, a patch, and/or other connected display-enabled article. This may include smart articles as described above and/or other articles.

The images rendered on a display may be part of a video or may be still images. In a video format, the rendered images may be presented in real-time as the sensed data is received. For example, in some embodiments, a digital three-dimensional (3D) model of a person's face may be built and then rendered for display based on the sensed data while using textures generated from images of the person's face. In a still image format, once an image is selected for display, possibly via a classification technique as described above, the image may be displayed for a period of time commensurate to a corresponding utterance or emotion. A current image may be replaced by fading into a next image for display thereby simulating a transition. Further, images may be merged or interpolated to address a need for showing a person's mouth move while smiling or frowning.

In other embodiments, the mask display may not be a physical display integrated as part of a mask or disposed on the mask wearer. For example, consider a newscaster. A field reporter may wear a green screen mask (i.e., a mask that is just green). As video of the reporter is captured and corresponding sensed data is received, the system of the example embodiment may generate corresponding digital images (e.g., chroma content, etc.) that are superimposed on the green mask thereby rendering the reporter's face for broadcast. Another example may include using a projector system that projects images on the mask of a live actor. As an example, the central control station 102 of FIG. 1 and/or other device may be implemented as a projector and project or superimpose images on a projector screen or a green screen of one or more smart articles (e.g., the smart article 400 of FIG. 4). Still further, the display may be coupled with a robot, possibly a telepresence interface, where the robot displays a face corresponding to a controller.

The disclosed mask system examples may also be used with respect to face recognition. The displayed images of a person's face may be augmented to include additional features that aid in recognizing a person's face, such additional features may include stronger contrast on key facial features or descriptors to facilitate analysis by other computing software. The reverse also has utility. The displayed images may be augmented to reduce or disrupt facial recognition software. For example, the displayed images may correspond to cartoon versions of a person's face or may de-enhance recognition features of the person's face thereby increasing privacy of the mask wearer.

In some industries, face recognition technologies are used to identify a person based on features in an image: eyes, nose, mouth, etc. The disclosed approach seeks to leverage these types of known techniques to create a collection of images of a person for display on a mask.

The movie industry leverages motion capture where actors wear green suits or wear identifiable markers. As the actor moves, the markers are tracked. A digital avatar may be manipulated to move in the same way as the actor by mapping the avatar's movements to the tracked markers. Further, digital or graphic renderings may be superimposed on the actor's bodies using traditional green screen techniques. Similar to the face recognition, tracking markers may be leveraged to create a mapping between movements of a person's face and a corresponding rendering.

Synchronizing a rendering of lips of video game characters to dialogs has been used by video games to create a more realistic experience for game players. For example, U.S. Pat. No. 6,307,576 to Rosenfeld describes such techniques. However, the example rendering of lips as disclosed herein are two-dimensional (2D) constructs on articles.

As another example, sensed movement and/or other modalities may be combined to create a rendering on a mask. The masks may include graphene filters and graphene sensors. The masks may include graphene for protection and filtering, as well as for sensing, for example, movements. Graphene may be implemented as part of sensor material. While graphene may be used as a biosensor, graphene's electrical properties allow graphene to be used in sensors disclosed herein to measure stress and/or strain. When graphene sensors are strained, the sensors generate an electrical signal that is amplified and detected. In one embodiment, a graphene material is not used as both a sensor and a filter at a same time. The same graphene material may be used as a sensor or a filter at any instance in time. Different graphene material layers may be provided to perform respectively as a sensor and a filter.

Sensors attached to the face may be used to determine aspects of a person's emotions. For example, graphene sensors may be used to determine emotions, which may include stretchable and/or flexible sensors. Facial movement may be detected in real-time using these sensors.

Some traditional masks are clear such that a person's face can be seen while wearing one of the masks. However, such masks are not flexible. The examples provided herein provide masks that may be flexible and allow others to see facial expressions on a display and/or elsewhere as described above.

The face masks and other articles disclosed herein may be used for various purposes and in various implementations. This includes use of smart masks, during, for example, a COVID pandemic. Other examples are referred to below and include military, police/fire, motorcycle, theater, movie, medical, novelty, religion, sports, service industries, hearing impaired, autism, new casting, and computer game example applications.

The military often is called upon to wear masks while interacting with civilians. The disclosed techniques may be used to soften the appearance of military personnel and make them more accessible to civilians. A police use case largely follows the military use case.

Many motorcyclists wear full head covering helmets. The disclosed techniques may provide for displaying (or projecting) a cyclist's expressions on a surface of a helmet. As yet another example, actors may leverage a purpose built face mask that covers portions or an entire face such that an actor may appear as another person or appear with dynamic makeup.

Similar to the theater example, during motion capture sessions where a person wears a motion capture suit, the person's expressions may be captured and mapped to a predetermined feature set using the examples disclosed herein.

As another example, a medical healthcare professional may implement some of the examples disclosed herein. As an example, high fidelity images of the professional may be taken and provided to aid in easing a patient's experience.

Yet another use case (novelty case) may include creating purpose built Holiday (e.g., Halloween) masks having desired, novelty driven features. Further, one may monetize the disclosed techniques by selling novelty animations or perhaps celebrity images for a fee or subscription. As a further example, the techniques may be applied to, for example, a burqa or niqab if permissible.

The examples may also be applied to helmets used in full helmet sports, such as American football. Aspects of a player's face may be displayed on a helmet. The displays on the helmets may be used for controlling parts of the game. Services industries such as restaurants would likely benefit from the disclosed masks and articles to allow people to feel more comfortable during dining experiences.

People interacting with the hearing impaired may wear the disclosed masks and/or articles. The hearing-impaired person may see the person's mouth on one of the displays move in a more exaggerated manner than actually being moved to improve lip reading. The mask may display text corresponding to the person's speech. The mask may display an emoticon to match a person's mood and/or other emotions. Further, a hearing impaired person could use a set of gloves having sensors as discussed above with respect to the mask. As the hearing impaired person uses their hands to communicate via sign language, their mask could display images representing mouth positions for the words they are signing. Yet further, the mask could be instrumented to generate corresponding audio signals via a speaker where the audio signals comprise a digital voice speaking the corresponding words. Similar to the hearing-impaired approach, a mask may be used to display a person's emotional state such that people with autism are able to quickly interpret another person's emotion. Alternatively, a person could use the disclosed system to practice emoting to ensure they are properly providing social cues. One should appreciate that the smart mask could display more than one image modality. For example, the mask could display a person's mouth movements, corresponding text, emoticons, or other such features at the same time.

During the COVID-19 pandemic, many newscasters have worn masks while reporting to the public. The disclosed examples may be used to display a newscaster's mouth as the newscaster provides televised reports. The smart mask may also operate as a game controller where sensor data is used to determine control over gaming elements. Further, the smart mask may be used in virtual reality (VR) systems, where a person's facial movements are rendered in the VR setting on the wearer's VR avatar. In such embodiments, the mask technology disclosed herein can be integrated into a VR headset, coupled to the VR headset, or coupled to the VR computing system. In such an arrangement, a VR user could have their avatars displayed with the user's current mouth positions.

Yet another aspect of the inventive technology includes leveraging a location sensor (e.g., GPS sensor, internal movement unit, SLAM, vSLAM, wireless triangulation device, etc.) to determine a location of the smart article. Location data can be leveraged to select one or more language modules for translation purposes. For example, if a person speaks English, but is wearing a mask in Italy, the displayed images could include Italian translated text. U.S. Pat. No. 10,367,652 describes location-based techniques for selecting device interaction domains that can be adapted for use with the inventive subject matter. Further, location could be used to select a desired image set. If a person is located in an informal setting (e.g., at a park, ballgame, etc.), the displayed images of mouth movements might correspond to a purchased images of a favorite cartoon character, while when the person is located in a formal setting (e.g., an office, etc.), the images selected for display might include the person's actual face images. This can be achieved via a look up table, mapping the location data to a geo-fenced area, or other form of indexing.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A smart mask system comprising:

a first material layer configured to cover a portion of a face of a person;

at least one display connected to the first material layer and configured to display images;

a location sensor configured to obtain location data associated with the smart mask system; and a computer-based control module comprising:

at least one non-transitory memory storing a plurality of indexed image sets and software instructions, wherein each of the plurality of image sets are indexed based on location data; and at least one processor coupled with the at least one non-transitory memory and that performs the following operations upon execution of the software instructions:

determining a context based on a location derived from the location data obtained from the location sensor;

selecting an indexed image set from the plurality of indexed image sets based on at least the determined context and the location data, wherein selecting the indexed image set includes selecting the indexed image set via at least one of a look up or a mapping of location data to a defined area, selecting a formal image when the determined context is a formal context, and selecting an informal image when the determined context is an informal context; and rendering at least one image from the location-based selected image set on the display, wherein the display comprises multiple light emitting diodes configured to render a visual digital image covering at least a portion of the first material layer, wherein a first indexed image set of the plurality of indexed image sets comprises actual face images of the person, and the actual face images of the person are selected for rendering on the display in response to the determined context being the formal context.

2. The smart mask system of claim 1, wherein the formal context corresponds to an office location.

3. The smart mask system of claim 1, wherein the informal context corresponds to at least one of a park location and a sports venue location.

4. The smart mask system of claim 1, wherein:

a second indexed image set of the plurality of indexed image sets comprises cartoon character images; and the cartoon character images are selected for rendering on the display in response to the determined context being the formal context.

5. The smart mask system of claim 1, wherein the location data is derived from at least one of the following: a GPS sensor, an internal movement unit, SLAM data, vSLAM data, and a wireless triangulation device.

6. The smart mask system of claim 1, wherein the computer-based control module is further configured to select a language module based on the location.

7. The smart mask system of claim 6, wherein the computer-based control module is configured to display translated text based on the selected language module.

8. The smart mask system of claim 1, further comprising a plurality of sensors configured to detect facial movements of the person.

9. The smart mask system of claim 8, wherein the plurality of sensors comprises at least one of piezoelectric sensors, thermal sensors, stretch sensors, and compression sensors.

10. The smart mask system of claim 8, wherein the computer-based control module is configured to render the at least one image based on both the detected facial movements and the determined context.

11. The smart mask system of claim 1, wherein the at least one display comprises a high-resolution display having a resolution greater than 70 dots per inch.

12. The smart mask system of claim 1, wherein the at least one display comprises a low-resolution LED array having a resolution less than 70 dots per inch.

13. The smart mask system of claim 1, wherein the at least one display permits airflow.

14. The smart mask system of claim 1, further comprising at least one filter comprising antimicrobial material.

15. The smart mask system of claim 1, wherein the computer-based control module is configured to automatically switch between indexed image sets when a change in location is detected.

16. The smart mask system of claim 1, further comprising a wireless transceiver allowing communications with external devices.

17. The smart mask system of claim 16, wherein the wireless transceiver operates within a personal area network.

18. The smart mask system of claim 1, wherein the computer-based control module is configured to modify the rendered at least one image to thereby reduce facial recognition.

* * * * *